US009994758B2

(12) United States Patent
Coates

(10) Patent No.: US 9,994,758 B2
(45) Date of Patent: *Jun. 12, 2018

(54) MICROBIAL METABOLISM OF CHLORINE OXYANIONS AS A CONTROL OF BIOGENIC HYDROGEN SULFIDE PRODUCTION

(71) Applicant: The Regents of the University of California, Oakland, CA (US)

(72) Inventor: John D. Coates, Walnut Creek, CA (US)

(73) Assignee: The Regents of the University of California, Oakland, CA (US)

(*) Notice: Subject to any disclaimer, the term of this patent is extended or adjusted under 35 U.S.C. 154(b) by 63 days.

This patent is subject to a terminal disclaimer.

(21) Appl. No.: 15/160,680

(22) Filed: May 20, 2016

(65) Prior Publication Data

US 2016/0369156 A1 Dec. 22, 2016

Related U.S. Application Data

(63) Continuation of application No. 14/123,073, filed as application No. PCT/US2012/040273 on May 31, 2012, now Pat. No. 9,365,845.

(60) Provisional application No. 61/493,367, filed on Jun. 3, 2011.

(51) Int. Cl.
| | |
|---|---|
| *C09K 8/532* | (2006.01) |
| *C07K 14/195* | (2006.01) |
| *C12N 1/00* | (2006.01) |
| *C12N 9/99* | (2006.01) |

(52) U.S. Cl.
CPC ............ *C09K 8/532* (2013.01); *C07K 14/195* (2013.01); *C12N 1/00* (2013.01); *C12N 9/99* (2013.01); *C09K 2208/20* (2013.01)

(58) Field of Classification Search
CPC ...... C09K 8/532; C09K 2208/20; C12N 9/99; C12N 1/00; C07K 14/195
See application file for complete search history.

(56) References Cited

U.S. PATENT DOCUMENTS

| | | | | |
|---|---|---|---|---|
| 2,912,378 | A | 11/1959 | Bernard | |
| 4,818,412 | A | 4/1989 | Conlan | |
| 9,365,845 | B2 * | 6/2016 | Coates | C07K 14/195 |
| 2009/0258349 | A1 | 10/2009 | Hristova et al. | |
| 2010/0216217 | A1 | 8/2010 | Hendrickson et al. | |
| 2010/0216219 | A1 | 8/2010 | Hendrickson et al. | |
| 2012/0255726 | A1 | 10/2012 | Lomans | |

FOREIGN PATENT DOCUMENTS

| | | |
|---|---|---|
| CN | 101979825 A | 2/2011 |
| WO | 2010096515 A1 | 8/2010 |

OTHER PUBLICATIONS

Final Office Action received for U.S. Appl. No. 14/123,073, dated Dec. 1, 2015, 19 pages.
International Preliminary Report on Patentability received for PCT Patent Application No. PCT/US2012/040273, dated Dec. 19, 2013, 7 pages.
International Search Report and Written Opinion received for PCT Patent Application No. PCT/US2012/040273, dated Aug. 1, 2012, 10 pages.
Non-Final Office Action received for U.S. Appl. No. 14/123,073, dated Apr. 22, 2015, 20 pages.
Notice of Allowance received for U.S. Appl. No. 14/123,073, dated Feb. 16, 2016, 9 pages.
Office Action received for Chinese Patent Application No. 201280036406.4, dated Feb. 2, 2015, 17 pages (9 pages of English Translation and 8 pages of Official Copy).
Office Action received for European Patent Application No. 12727500.6, dated Sep. 29, 2014, 3 pages.
Requirement for Restriction received for U.S. Appl. No. 14/123,073, dated Nov. 7, 2014, 10 pages.
Abascal et al., "ProtTest: Selection of Best-Fit Models of Protein Evolution", Bioinformatics, vol. 21, No. 9, 2005, pp. 2104-2105.
Achenbach et al., "Dechloromonas Agitata Gen. Nov., Sp. Nov. and Dechlorosoma Suillum Gen. Nov., Sp. Nov., Two Novel Environmentally Dominant (per)Chlorate-Reducing Bacteria and their Phylogenetic Position", International Journal of Systematic and Evolutionary Microbiology, vol. 51, 2001, pp. 527-533.
Altsehul et al., "Basic Local Alignment Search Tool", Journal of Molecular Biology, vol. 215, 1990, pp. 403-410.
Altschul, S. et al., "Gapped BLAST and PSI-BLAST: A New Generation of Protein Database Search Programs", Nucleic Acids Research, vol. 25, No. 17, 1997, pp. 3389-3402.
Bender et al., "Identification, Characterization, and Classification of Genes Encoding Perchlorate Reductase", Journal of Bacteriology, vol. 187, No. 15, Aug. 2005, pp. 5090-5096.
Bender et al., "Metabolic Primers for Detection of (Per)chlorate-Reducing Bacteria in the Environment and Phylogenetic Analysis of cld Gene Sequences", Applied and Environmental Microbiology, vol. 70, No. 9, Sep. 2004, pp. 5651-5658.
Bender et al., "Sequencing and Transcriptional Analysis of the Chlorite Dismutase Gene of Dechloromonas Agitata and Its Use as a Metabolic Probe", Applied and Environmental Microbiology, vol. 68, No. 10, Oct. 2002, pp. 4820-4826.
Bruce et al., "Reduction of (per)chlorate by a Novel Organism Isolated from Paper Mill Waste", Environmental Microbiology, vol. 1, No. 4, Aug. 1999, pp. 319-329.
Chaudhuri et al., "Environmental Factors That Control Microbial Perchlorate Reduction", Applied and Environmental Microbiology, vol. 68, No. 9, Sep. 2002, pp. 4425-4430.
Cline, Joel D., "Spectrophotometric Determination of Hydrogen Sulfide in Natural Waters", Limnology and Oceanography, vol. 14, 1969, pp. 454-458.
Coates et al., "Anaerobic Benzene Oxidation Coupled to Nitrate Reduction in Pure Culture by Two Strains of Dechloromonas", Nature, vol. 411, Jun. 28, 2001, pp. 1039-1043.

(Continued)

*Primary Examiner* — Marsha Tsay
(74) *Attorney, Agent, or Firm* — Morrison & Foerster LLP

(57) ABSTRACT

The present disclosure relates to methods of controlling the sulfide ($S^{2-}$) content in systems, such as oil and gas reservoirs and pipelines, by the use of chlorine oxyanions and microorganisms with (per)chlorate-reducing activity.

16 Claims, 9 Drawing Sheets

(56) References Cited

OTHER PUBLICATIONS

Coates et al., "Anaerobic Hydrocarbon Degradation in Petroleum-Contaminated Harbor Sediments under Sulfate-Reducing and Artificially Imposed Iron-Reducing Conditions", Environmental Science and Technology, vol. 30, No. 9, 1996, pp. 2784-2789.

Coates et al., "Microbial Perchlorate Reduction: Rocket-Fuelled Metabolism", Nature Reviews Microbiology, vol. 2, Jul. 2004, pp. 569-580.

Coates et al., "The Microbiology of Perchlorate Reduction and Its Bioremediative Application", Perchlorate (Content only), 2006, pp. 279-295.

Coates et al., "Ubiquity and Diversity of Dissimilatory (Per)Chlorate-Reducing Bacteria", Applied and Environmental Microbiology, vol. 65, No. 12, Dec. 1999, pp. 5234-5241.

Corpet, Florence, "Multiple Sequence Alignment with Hierarchical Clustering", Nucleic Acids Research, vol. 16 No. 22, 1988, pp. 10881-10890.

Domínguez et al., "XerCD-Mediated Site-Specific Recombination Leads to Loss of the 57-Kilobase Gonococcal Genetic Island", Journal of Bacteriology, vol. 193, No. 2, Jan. 2011, pp. 377-388.

Eddy, Sean R., "Profile Hidden Markov Models", Bioinformatics Review, vol. 14, No. 9, 1998, pp. 755-763.

Fukuda et al., "Dynamic Analysis of a Genomic Island in Magnetospirillum Sp. Strain AMB-1 Reveals how Magnetosome Synthesis Developed", FEBS Letters, vol. 580, 2006, pp. 801-812.

Gao et al., "Overexpression in *E. coli* of Perchlorate Reductase, An Oxygen-Sensitive Enzyme from Dissimilatory Perchlorate-Reducing Bacteria", Abstracts of the General Meeting of the American Society for Microbiology, vol. 108, 2008, 1 page.

Gieg et al., "Biological Souring and Mitigation in Oil Reservoirs", Appl. Microbiol. Biotechnol. vol. 92, Aug. 20, 2011, pp. 263-282.

Guindon et al., "A Simple, Fast, and Accurate Algorithm to Estimate Large Phylogenies by Maximum Likelihood", Systematic Biology, vol. 52, No. 5, 2003, pp. 696-704.

Higgins et al., "CLUSTAL: A Package for Performing Multiple Sequence Alignment on a Microcomputer", Gene, vol. 73, 1988, pp. 237-244.

Higgins et al., "Fast and Sensitive Multiple Sequence Alignments on a Microcomputer", Cabios Communications, vol. 5, No. 2, 1989, pp. 151-153.

Huang et al., "Parallelization of a Local Similarity Algorithm", Cabios, vol. 8, No. 2, 1992, pp. 155-165.

Hubert et al., "Oil Field Souring Control by Nitrate-Reducing Sulfurospuillum spp. that Outcompete Sulfate-Reducing Bacteria for Organic Electron Donors", Applied and Environmental Microbiology, vol. 73, No. 8, Apr. 2007, pp. 2644-2652.

Ippen-Ihler et al., "The Conjugation System of F, The Fertility Factor of *Escherichia Coli*", Annual Review of Genetics, vol. 20, Dec. 1986, pp. 593-624.

Juhas et al., "Genomic Islands: Tools of Bacterial Horizontal Gene Transfer and Evolution", FEMS Microbiol Reviews, vol. 33, 2009, pp. 376-393.

Karlin et al., "Applications and Statistics for Multiple High-Scoring Segments in Molecular Sequences", Proceedings of the National Academy of Sciences, vol. 90, Jun. 1993, pp. 5873-5877.

Karlin et al., "Methods for Assessing the Statistical Significance of Molecular Sequence Features by Using General Scoring Schemes", Proceedings of the National Academy of Sciences of the United States of America, vol. 87, No. 6, Mar. 1990, pp. 2264-2268.

Kirk et al., "Perchlorate and Iodide in Dairy and Breast Milk", Environmental Science & Technology, vol. 39, No. 7, 2005, pp. 2011-2017.

Kounaves et al., "Discovery of Natural Perchlorate in the Antarctic Dry Valleys and its Global Implications", Environmental Science & Technology, vol. 44 (Abstract only), 2010, pp. 2360-2364.

Lawrence et al., "The Effect of Short-Term Low-Dose Perchlorate on Various Aspects of Thyroid Function", Thyroid, vol. 10, No. 8, 2000, pp. 659-663.

Lima et al., "HAMAP: A Database of Completely Sequenced Microbial Proteome Sets and Manually Curated Microbial Protein Families in UniProtKB/Swiss-Prot", Nucleic Acids Research, vol. 37, 2009, pp. D471-D478.

Lovley et al., "Deep Subsurface Microbial Processes", Reviews of Geophysics, vol. 33, No. 3, Aug. 1995, pp. 365-381.

Melnyk et al., "Identification of a Perchlorate Reduction Genomic Island with Novel Regulatory and Metabolic Genes", Applied and Environmental Microbiology, vol. 77, No. 20, Oct. 2011, pp. 7401-7404.

Münch et al., "Virtual Footprint and PRODORIC: An Integrative Framework for Regulon Prediction in Prokaryotes", Bioinformatics, vol. 21, No. 22, 2005, pp. 4187-4189.

Myers et al., "Optimal Alignments in Linear Space", Cabios, vol. 4, 1988, 13 pages.

Needleman et al., "A General Method Applicable to the Search for Similarities in the Amino Acid Sequence of Two Proteins", Journal of Molecular Biology, vol. 48, 1970, pp. 443-453.

O'Connor et al., "Universal Immunoprobe for (Per)Chlorate-Reducing Bacteria", Applied and Environmental Microbiology, vol. 68, No. 6, Jun. 2002, pp. 3108-3113.

Pearson et al., "Improved Tools for Biological Sequence Comparison", Proceedings of the National Academy of Sciences, vol. 85, Apr. 1988, pp. 2444-2448.

Pearson, William R., "Using the FASTA Program to Search Protein and Dna Sequence Databases", Methods in Molecular Biology, vol. 24, 1994, pp. 307-331.

Sanchez et al., "Perchlorate and Nitrate in Leafy Vegetables of North America", Environmental Science & Technology, vol. 39, No. 24, 2005, pp. 9391-9397.

Semsey et al., "Site-Specific Integrative Elements of Rhizobiophage 16-3 Can Integrate into Proline tRNA (CGG) Genes in Different Bacterial Genera", Journal of Bacteriology, vol. 184, No. 1, Jan. 2002, pp. 177-182.

Smith et al., "Comparison of Biosequences", Advances in Applied Mathematics, vol. 2, 1981, pp. 482-489.

Sun et al., "Behavioral Response of Dissimilatory Perchlorate-Reducing Bacteria to Different Electron Acceptors", Appl Microbiol Biotechnol, vol. 84, 2009, pp. 955-963.

Sunde et al., "Microbial Control of Hydrogen Sulfide Production in Oil Reservoirs", Petroleum Microbiology, ASM Press (Content only), 2005, pp. 201-214.

Thrash et al., "Electrochemical Stimulation of Microbial Perchlorate Reduction", Environmental Science & Technology, vol. 41, No. 5, 2007, pp. 1740-1746.

Thrash et al., "Magnetospirillum Bellicus Sp. Nov., A Novel Dissimilatory Perchlorate-Reducing Alphaproteobacterium Isolated from a Bioelectrical Reactor", Applied and Environmental Microbiology, vol. 76, No. 14, Jul. 2010, pp. 4730-4737.

Thrash et al., "Review: Direct and Indirect Electrical Stimulation of Microbial Metabolism", Environmental Science & Technology, vol. 42, No. 11, 2008, pp. 3921-3931.

Trump et al., "Thermodynamic Targeting of Microbial Perchlorate Reduction by Selective Electron Donors", The ISME Journal, vol. 3, 2009, pp. 466-476.

Van et al., "Purification and Characterization of Chlorite Dismutase: A Novel Oxygen-Generating Enzyme", Archives of Microbiology, vol. 166, No. 5, Nov. 1996, pp. 321-326.

Vance et al., "Reservoir Souring: Mechanisms and Prevention", Petroleum Microbiology, ASM Press (Content only), 2005, pp. 123-142.

"Azospira", available at <http://ncbi.nlm.nih.gov/Taxonomy/Browser/wwwtax.cgi?mode=Info&id=146937&1>, retrieved on Apr. 15, 2015, 2 pages.

"Dechloromonas Aromatica: Daro_2580", available at <http://www.genome.jp/dbget-bin/www_bget?dar:Daro_2580>, retrieved on Apr. 15, 2015, 1 page.

"Nitrates and Nitrates: Answers to Frequently Asked Health Questions", Bureau of Environmental Health, Health Assessment Section, last viewed on Apr. 15, 2015, 2 pages.

"Ontiveros-Valencia Dissertation", May 2014.

(56) References Cited

OTHER PUBLICATIONS

Coates et al. "Hydrocarbon Bioremediative Potential of (Per)Chlorate-Reducing Bacteria", Bioremediation Journal, vol. 3, No. 4, 1999, pp. 323-334.
EPA Guidance Manual "Chapter 4: Chlorine Dioxide", Alternative Disinfectants and Oxidants Guidance Manual, Apr. 1999, pp. 4-1-4-41.
Goblirsch et al. "Structural Features Promoting Dioxygen Production by Dechloromonas Aromatica Chlorite Dismutase", J Biol Inorg Chem., vol. 15, No. 6, Aug. 2010, pp. 879-888.
Min et al. "Perchlorate Removal in Sand and Plastic Media Bioreactors", Water Research, vol. 38, 2004, pp. 47-60.
Postgate J. R. "Competitive and Non-competitive Inhibitors of Bacterial Sulphate Reduction", J. Gen. Microbiol., vol. 6, 1952, pp. 128-142.
Rao, Balaji "Natural Perchlorate and Chlorate in the Environment: An Investigation of their Occurrence and Formation Processes", A Dissertation in Civil Engineering submitted to the Graduate Faculty of Texas Tech University, Dec. 2010, 140 pages.
Taniai et al. "Monitoring of Hydrogen Peroxide, Nitrate and Nitrite in Rain Water", Analytical Sciences, vol. 16, Mar. 2000, pp. 275-281.
Telang et al. "Characterization of the Diversity of Sulfate-Reducing Bacteria in Soil and Mining Waste Water Environments by Nucleic Acid Hybridization Techniques", Canadian Journal of Microbiology, vol. 40, No. 11, Nov. 1994 pp. 955-964.
Tsang et al. "Sulfate-Reducing Pathway in *Escherichai Coli* Involving Bound Intermediates", Journal of Bacteriology, vol. 125, No. 3, Mar. 1976, pp. 923-933.
Voordouw et al. "NACE International", Corrosion, Conference Paper, Mar. 28-Apr. 1, 2004.
Wind et al. "Sulfate-reducing Bacteria in Rice Field Soil and on Rice Roots", Systematic and Applied Microbiology, vol. 22, No. 2, 1999, pp. 269-279.
Office Action received for Australian Patent Application No. 2012262115, dated May 6, 2016, 3 pages.
Decision to Grant received for European Patent Application No. 12727500.6, dated Jun. 9, 2016, 2 pages.
Intention to Grant received for European Patent Application No. 12727500.6, dated Dec. 22, 2015, 6 pages.
Office Action received for European Patent Application No. 12727500.6, dated Jun. 29, 2015, 69 pages.
Office Action received for Chinese Patent Application No. 201280036406.4, dated Aug. 27, 2015, 8 pages (4 pages of English Translation and 4 pages of Official Copy).
Office Action received for Chinese Patent Application No. 201280036406.4, dated Feb. 5, 2016, 6 pages (3 pages of English Translation and 3 pages of Official copy).
Office Action received for Egyptian Patent Application No. 2013001855, dated Mar. 29, 2015, 5 pages (English Translation only).
Office Action received for Eurasian Patent Application No. 201391814/28 dated Dec. 3, 2015, 3 pages (1 page of English Translation and 2 pages of Official copy).
Office Action Received for Eurasian Patent Application No. 201391814/28, dated Apr. 21, 2015, 6 pages (3 pages of English Translation and 3 pages of Official copy).
Notice of Allowance Received for Mexican Patent Application No. MX/a/2013/014115, dated Feb. 10, 2016, 3 pages (2 pages of English Translation and 1 page of Official copy).
Notice of Acceptance received for Nigerian Patent Application No. NG/C/2013/809, dated Jun. 3, 2015, 1 page.

* cited by examiner

SRB: SULFATE-REDUCING BACTERIA

DPRB: DISSIMILATORY (PER) CHLORATE-REDUCING BACTERIA

REMOVE FROM SYSTEM

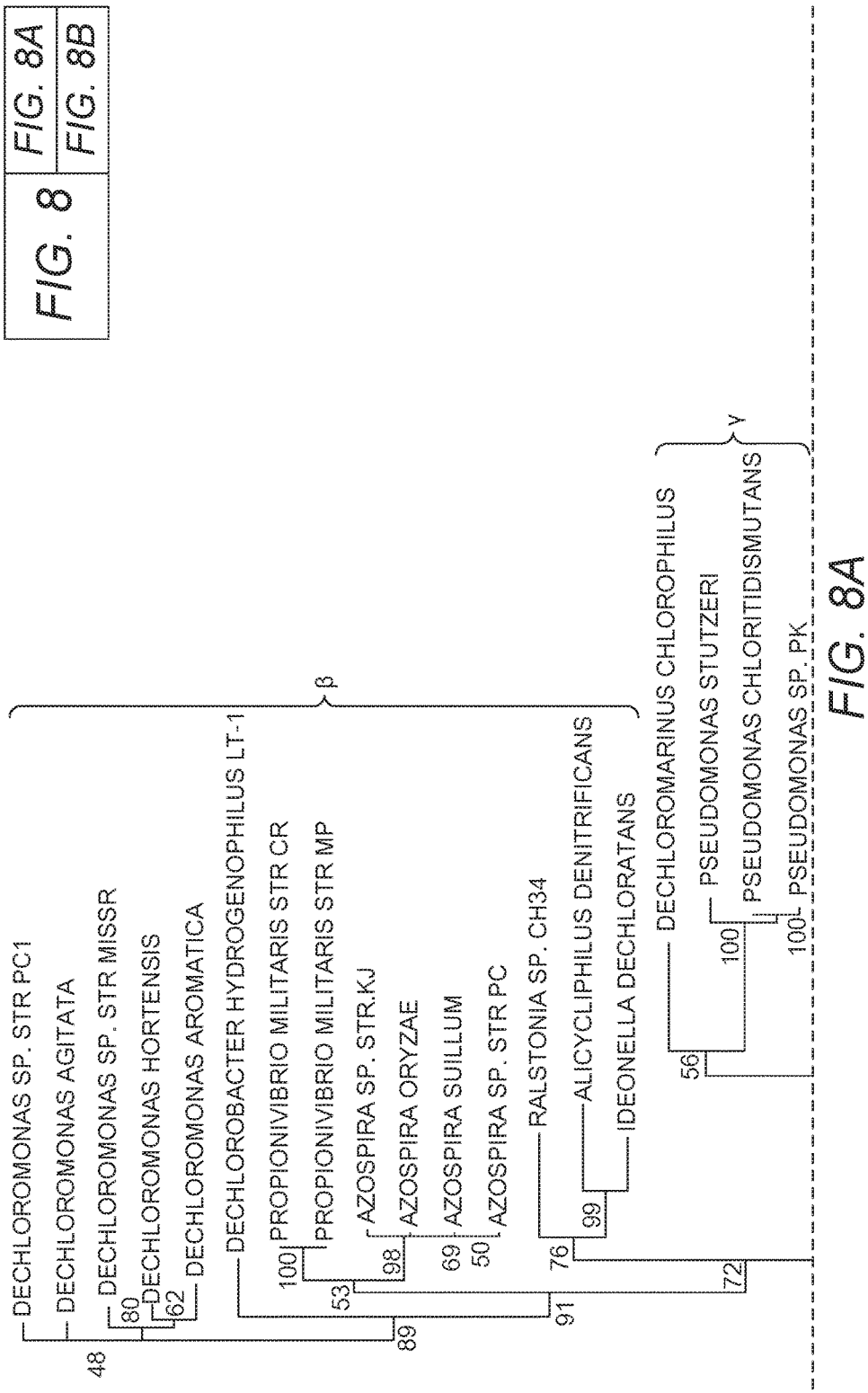

MICROBIAL METABOLISM OF CHLORINE OXYANIONS AS A CONTROL OF BIOGENIC HYDROGEN SULFIDE PRODUCTION

CROSS-REFERENCE TO RELATED APPLICATIONS

This application is a Continuation of U.S. application Ser. No. 14/123,073, internationally filed on May 31, 2012, now issued as U.S. Pat. No. 9,365,845, which is a U.S. National Phase patent application of PCT/US2012/040273, filed May 31, 2012, which claims the benefit of U.S. Provisional Application No. 61/493,367, filed Jun. 3, 2011, each of which are hereby incorporated by reference, in their entirety.

FIELD

The present disclosure relates to methods of controlling the sulfide ($S^{2-}$) content in systems, such as oil and gas reservoirs and pipelines, by the use of chlorine oxyanions and microorganisms with (per)chlorate-reducing activity.

BACKGROUND

The generation of hydrogen sulfide ($H_2S$) results in a variety of corrosion problems. For example, sulfidogenesis results in a variety of oil recovery problems, including oil reservoir souring, contamination of crude oil, metal corrosion, and the precipitation of metal sulfides which can subsequently plug pumping wells.

An important aspect of microbial enhanced-hydrocarbon recovery (MEHR) is control of reservoir souring. Reservoir souring is characterized by significant increases in $H_2S$ in production gas and soluble $HS^-$ in production fluids, typically after initiation of secondary recovery processes involving water injection. Although several abiotic mechanisms have been proposed as the cause of reservoir souring including thermochemical sulfate ($SO_4^{2-}$) reduction and pyrite ($FeS_2$) dissolution, it is now widely accepted that sulfate-reduction by dissimilatory sulfate-reducing bacteria (SRB) is primarily responsible for sulfide production in reservoir souring as a result of water flooding (Vance and Thrasher, *Petroleum Microbiology*, eds B. Ollivier & M. Magot, ASM Press, 2005).

Sour service metallurgy for wells, pipelines, and pump systems carry an estimated cost premium of 2% of total project costs at project initiation but may be an order of magnitude higher if retrofitting is required (Al-Rasheedi et al., *SPE Middle East Oil Show*, Society of Petroleum Engineers). Sour production facilities also entail additional costs associated with prevention of operator exposure to toxic $H_2S$; control of oil-wet iron sulfide pads that reduce oil-water separator performance, management of iron sulfide solids that interfere with produced water cleanup and recycle, and accumulation of iron-sulfide deposits that may foul equipment and enhance equipment corrosion. In addition, revenue loss may result from limitations imposed on pumping high volumes of oil and gas with excessive $H_2S$ concentrations through export lines to ensure system integrity (Vance and Thrasher, *Petroleum Microbiology*, eds B. Ollivier & M. Magot, ASM Press, 2005).

Effort has focused on mechanisms by which $H_2S$ generation from dissimilatory sulfate-reducing metabolism can be inhibited. Significant research has focused on thermodynamic inhibition of SRB activity by the addition of nitrate to the injection waters. Thermodynamic considerations indicate that microbial nitrate reduction is energetically more favorable than Fe(III)-reduction, sulfate-reduction, or methanogenesis and should therefore occur first (Coates and Achenbach, *Manual of Environmental Microbiology*, eds C. J. Hurst et al., 719-727, ASM Press, 2001; and Lovely and Chapelle, *Reviews of Geophysics* 33, 365-381, 1995). For example the Gibbs free energy for the anaerobic degradation of toluene coupled to nitrate-reduction ($\Delta G_o'=-3,554$ kJmol$^{-1}$ toluene) is significantly higher than that coupled to sulfate-reduction ($\Delta G_o'=-205$ kJmol$^{-1}$ toluene). Thus, the addition of excess amounts of nitrate should result in the preferential utilization of this electron acceptor and the selective inhibition of sulfate-reduction.

However, thermodynamic preferential use of nitrate over sulfate is not mutually exclusive in a system unlimited for electron donors, such as in an oil reservoir where hydrocarbon reserves represent an inexhaustible supply of biodegradable carbon to active microbial communities (Coates and Achenbach, *Manual of Environmental Microbiology*, eds C. J. Hurst et al., 719-727, ASM Press, 2001; and Van Trump and Coates, *Isme J* 3, 466-476, 2009). As such, while the presence of nitrate will slow down sulfate-reduction, it will not completely inhibit sulfate metabolism. Furthermore, the results of previous studies suggest that addition of a thermodynamically more favorable electron acceptor, such as Fe(III), may not be enough to completely inhibit sulfate-reduction once an active SRB community is established (Coates et al., *Environmental Science and Technology* 30, 2784-2789, 1996).

Thus, there exists a need to develop an economic and efficient method of regulating the amount of $S^{2-}$ produced by microbial sulfate-reduction in systems such as during oil recovery.

BRIEF SUMMARY

In order to meet the above needs, the present disclosure provides methods and compositions for decreasing the amount of one or more sulfide-containing compounds in oil- or gas-containing systems by using (per)chlorate-reducing bacteria that oxidize sulfide-containing compounds.

Accordingly, in certain embodiments, the present disclosure relates to a method of decreasing the amount of one or more sulfide-containing compounds in a system, by: a) providing a system containing one or more sulfate-reducing bacteria and one or more (per)chlorate-reducing bacteria; and b) adding a composition containing one or more chlorine oxyanions to the system, or one or more compounds which yield the one or more chlorine oxyanions upon addition to the system, at a concentration sufficient to stimulate (per)chlorate-reducing activity of the (per)chlorate-reducing bacteria, thereby decreasing the amount of the one or more sulfide-containing compounds in the system. In some embodiments, the method further includes adding one or more per(chlorate)-reducing bacteria to the system.

Other aspects of the present disclosure relate to a method of inhibiting sulfidogenesis in a system, by: a) providing a system containing one or more sulfate-reducing bacteria; and b) adding a composition containing one or more chlorine oxyanions to the system, or one or more compounds which yield the one or more chlorine oxyanions upon addition to the system, at a concentration sufficient to inhibit sulfate-reducing activity of the sulfate-reducing bacteria, thereby inhibiting sulfidogenesis in the system. In some embodiments, the method further includes adding one or more per(chlorate)-reducing bacteria to the system.

Other aspects of the present disclosure relate to a method of decreasing the amount of one or more sulfide-containing compounds in a system, by: a) providing a system containing one or more sulfate-reducing bacteria; b) adding one or more (per)chlorate-reducing bacteria; and c) adding a composition containing one or more chlorine oxyanions, or one or more compounds which yield the one or more chlorine oxyanions upon addition to the system, at a concentration sufficient to stimulate (per)chlorate-reducing activity of the (per)chlorate-reducing bacteria, thereby decreasing the amount of the one or more sulfide-containing compounds in the system.

In certain embodiments that may be combined with any of the preceding embodiments, the one or more (per)chlorate-reducing bacteria contain one or more recombinant nucleic acids selected from a nucleic acid that is at least 70%, 75%, 80%, 85%, 90%, 95%, 99%, or 100% identical to perA (Daro_2584); a nucleic acid that is at least 70%, 75%, 80%, 85%, 90%, 95%, 99%, or 100% identical to perB (Daro_2583); a nucleic acid that is at least 70%, 75%, 80%, 85%, 90%, 95%, 99%, or 100% identical to perC (Daro_2582); a nucleic acid that is at least 70%, 75%, 80%, 85%, 90%, 95%, 99%, or 100% identical to perD (Daro_2581); a nucleic acid that is at least 70%, 75%, 80%, 85%, 90%, 95%, 99%, or 100% identical to cld (Daro_2580); a nucleic acid that is at least 70%, 75%, 80%, 85%, 90%, 95%, 99%, or 100% identical to moaA (Daro_2577); a nucleic acid that is at least 70%, 75%, 80%, 85%, 90%, 95%, 99%, or 100% identical to QDH (Daro_2579); a nucleic acid that is at least 70%, 75%, 80%, 85%, 90%, 95%, 99%, or 100% identical to DHC (Daro_2578); a nucleic acid that is at least 70%, 75%, 80%, 85%, 90%, 95%, 99%, or 100% identical to HK (Daro_2586); a nucleic acid that is at least 70%, 75%, 80%, 85%, 90%, 95%, 99%, or 100% identical to RR (Daro_2585); a nucleic acid that is at least 70%, 75%, 80%, 85%, 90%, 95%, 99%, or 100% identical to PAS (Daro_2587); a nucleic acid that is at least 70%, 75%, 80%, 85%, 90%, 95%, 99%, or 100% identical to S (Daro_2590); a nucleic acid that is at least 70%, 75%, 80%, 85%, 90%, 95%, 99%, or 100% identical to AS (Daro_2589); a nucleic acid that is at least 70%, 75%, 80%, 85%, 90%, 95%, 99%, or 100% identical to OR1 (Daro_2591); a nucleic acid that is at least 70%, 75%, 80%, 85%, 90%, 95%, 99%, or 100% identical to OR2 (Daro_2592); and a nucleic acid that is at least 70%, 75%, 80%, 85%, 90%, 95%, 99%, or 100% identical to OR3 (Daro_2593). In certain embodiments that may be combined with any of the preceding embodiments, the one or more (per)chlorate-reducing bacteria are selected from *Ideonella; Dechloromarinus; Dechloromarinus* strain NSS; *Dechloromonas; Dechloromonas* strain FL2, FL8, FL9, CKB, CL, NM, MLC33, JM, HZ, CL24plus, CL24, CC0, RCB, SIUL, and MissR; *Dechloromonas aromaticae; Dechloromonas hortensis; Magnetospirillum; Magnetospirillum* strain SN1, WD, DB, and VDY; *Azospirillum; Azospirillum* strain TTI; *Azospira; Azospira* strain AH, Iso1, Iso2, SDGM, PDX, KJ, GR-1, and perclace; *Azospira suillum* strain PS; *Dechlorobacter; Dechlorobacter hydrogenophilus* strain LT-1; *Propionivibrio; Propionivibrio* strain MP; *Wolinella; Wolinella succinogenes* strain HAP-1; *Moorella; Moorella perchloratireducens; Sporomusa; Sporomusa* strain An4; *Proteus; Proteus mirabilis; Escherichia; Shewanella; Shewanella alga; Shewanella alga* strain ACDC; *Shewanella oneidensis* strain MR1; *Rhodobacter; Rhodobacter capsulatus; Rhodobacter sphaeroides; Alicycliphilus; Alicycliphilus denitroficans; Pseudomonas* strain PK, CFPBD, PDA, and PDB; and *Pseudomonas chloritidismutans*. In certain embodiments that may be combined with any of the preceding embodiments, the one or more (per)chlorate-reducing bacteria are *Dechloromonas aromaticae*. In certain embodiments that may be combined with any of the preceding embodiments, the one or more (per)chlorate-reducing bacteria are *Dechloromarinus* strain NSS. In certain embodiments that may be combined with any of the preceding embodiments, the one or more chlorine oxyanions are selected from hypochlorite, chlorine dioxide, chlorite, chlorate, perchlorate, and mixtures thereof. In certain embodiments that may be combined with any of the preceding embodiments, the one or more chlorine oxyanions are perchlorate. In certain embodiments that may be combined with any of the preceding embodiments, the method further includes adding nitrite. In certain embodiments, the nitrite is added at a concentration sufficient to inhibit the sulfate-reducing bacteria. In certain embodiments, the nitrite is added in amount sufficient to yield a chlorine oxyanion to nitrite ratio of at least 100:1. In certain embodiments, the nitrite is added to the system prior to adding the composition containing one or more chlorine oxyanions to the system, or the one or more compounds which yield the one or more chlorine oxyanions upon addition to the system. In certain embodiments that may be combined with any of the preceding embodiments, the method further includes a step of removing from the system, elemental sulfur produced by the one or more (per)chlorate-reducing bacteria. In certain embodiments that may be combined with any of the preceding embodiments, the one or more sulfide-containing compounds are hydrogen sulfide. In certain embodiments that may be combined with any of the preceding embodiments, the system is an oil reservoir, an oil-water separator, a wellhead, a gas pipeline or a gas supply line, a natural gas reservoir, a $CO_2$ storage well, a refinery, a gas-liquid separator, a chemical plant, or a desalination plant. In certain embodiments that may be combined with any of the preceding embodiments, the system is wastewater effluent from a pulp, paper, or textile mill, or wastewater effluent from a tannery. In certain embodiments that may be combined with any of the preceding embodiments, the method further includes adding molybdenum to the system.

Other aspects of the present disclosure relate to a system for refining a compound containing a sulfide contaminant, containing a container containing one or more (per)chlorate-reducing bacteria and a compound containing a sulfide contaminant, where the system does not contain a sulfide scrubber. Other aspects of the present disclosure relate to a chemical plant system for producing a compound containing a sulfide contaminant, containing a container containing one or more (per)chlorate-reducing bacteria and a compound containing a sulfide contaminant, where the system does not contain a sulfide scrubber. In certain embodiments, the compound containing a sulfide contaminant is selected from a gas, oil, a hydrocarbon, and a mixture thereof. Other aspects of the present disclosure relate to a wastewater treatment plant system for treating wastewater containing a sulfide contaminant, including a container with one or more (per)chlorate-reducing bacteria and sulfide-containing wastewater, where the system does not contain a sulfide scrubber.

In certain embodiments that may be combined with any of the preceding embodiments, the container further contains one or more chlorine oxyanions. In certain embodiments, the one or more chlorine oxyanions are selected from hypochlorite, chlorine dioxide, chlorite, chlorate, perchlorate, and a mixture thereof. In certain embodiments, the one or more chlorine oxyanions are perchlorate. In certain embodiments that may be combined with any of the preceding embodiments, the container further contains nitrite. In certain embodiments that may be combined with any of the preceding embodiments, the sulfide contaminant is hydrogen sulfide. In certain embodiments that may be combined with any of the preceding embodiments, the one or more (per)chlorate-reducing bacteria contain one or more recombinant nucleic acids selected from a nucleic acid that is at least 70%, 75%, 80%, 85%, 90%, 95%, 99%, or 100% identical to perA (Daro_2584); a nucleic acid that is at least 70%, 75%, 80%, 85%, 90%, 95%, 99%, or 100% identical to perB (Daro_2583); a nucleic acid that is at least 70%, 75%, 80%, 85%, 90%, 95%, 99%, or 100% identical to perC (Daro_2582); a nucleic acid that is at least 70%, 75%, 80%, 85%, 90%, 95%, 99%, or 100% identical to perD (Daro_2581); a nucleic acid that is at least 70%, 75%, 80%, 85%, 90%, 95%, 99%, or 100% identical to cld (Daro_2580); a nucleic acid that is at least 70%, 75%, 80%, 85%, 90%, 95%, 99%, or 100% identical to moaA (Daro_2577); a nucleic acid that is at least 70%, 75%, 80%, 85%, 90%, 95%, 99%, or 100% identical to QDH (Daro_2579); a nucleic acid that is at least 70%, 75%, 80%, 85%, 90%, 95%, 99%, or 100% identical to DHC (Daro_2578); a nucleic acid that is at least 70%, 75%, 80%, 85%, 90%, 95%, 99%, or 100% identical to HK (Daro_2586); a nucleic acid that is at least 70%, 75%, 80%, 85%, 90%, 95%, 99%, or 100% identical to RR (Daro_2585); a nucleic acid that is at least 70%, 75%, 80%, 85%, 90%, 95%, 99%, or 100% identical to PAS (Daro_2587); a nucleic acid that is at least 70%, 75%, 80%, 85%, 90%, 95%, 99%, or 100% identical to S (Daro_2590); a nucleic acid that is at least 70%, 75%, 80%, 85%, 90%, 95%, 99%, or 100% identical to AS (Daro_2589); a nucleic acid that is at least 70%, 75%, 80%, 85%, 90%, 95%, 99%, or 100% identical to OR1 (Daro_2591); a nucleic acid that is at least 70%, 75%, 80%, 85%, 90%, 95%, 99%, or 100% identical to OR2 (Daro_2592); and a nucleic acid that is at least 70%, 75%, 80%, 85%, 90%, 95%, 99%, or 100% identical to OR3 (Daro_2593). In certain embodiments that may be combined with any of the preceding embodiments, the one or more (per)chlorate-reducing bacteria are selected from *Ideonella*; *Dechloromarinus*; *Dechloromarinus* strain NSS; *Dechloromonas*; *Dechloromonas* strain FL2, FL8, FL9, CKB, CL, NM, MLC33, JM, HZ, CL24plus, CL24, CC0, RCB, SIUL, and MissR; *Dechloromonas aromaticae*; *Dechloromonas hortensis*; *Magnetospirillum*; *Magnetospirillum* strain SN1, WD, DB, and VDY; *Azospirillum*; *Azospirillum* strain TTI; *Azospira*; *Azospira* strain AH, Iso1, Iso2, SDGM, PDX, KJ, GR-1, and perclace; *Azospira suillum* strain PS; *Dechlorobacter*; *Dechlorobacter hydrogenophilus* strain LT-1; *Propionivibrio*; *Propionivibrio* strain MP; *Wolinella*; *Wolinella succinogenes* strain HAP-1; *Moorella*; *Moorella perchloratireducens*; *Sporomusa*; *Sporomusa* strain An4; *Proteus*; *Proteus mirabilis*; *Escherichia*; *Shewanella*; *Shewanella alga*; *Shewanella alga* strain ACDC; *Shewanella oneidensis* strain MR1; *Rhodobacter*; *Rhodobacter capsulatus*; *Rhodobacter sphaeroides*; *Alicycliphilus*; *Alicycliphilus denitroficans*; *Pseudomonas* strain PK, CFPBD, PDA, and PDB; and *Pseudomonas chloritidismutans*. In certain embodiments that may be combined with any of the preceding embodiments, the one or more (per)chlorate-reducing bacteria are *Dechloromonas aromaticae*. In certain embodiments that may be combined with any of the preceding embodiments, the one or more (per)chlorate-reducing bacteria are *Dechloromarinus* strain NSS.

Other aspects of the present disclosure relate to a container for storing a compound containing a sulfide contaminant, containing one or more (per)chlorate-reducing bacteria and a compound containing a sulfide contaminant.

In certain embodiments, the container further contains one or more chlorine oxyanions. In certain embodiments, the one or more chlorine oxyanions are selected from hypochlorite, chlorine dioxide, chlorite, chlorate, perchlorate, and a mixture thereof. In certain embodiments, the one or more chlorine oxyanions are perchlorate. In certain embodiments that may be combined with any of the preceding embodiments, the container further contains nitrite. In certain embodiments that may be combined with any of the preceding embodiments, the container is a $CO_2$ storage well. In certain embodiments that may be combined with any of the preceding embodiments, the sulfide contaminant is hydrogen sulfide. In certain embodiments that may be combined with any of the preceding embodiments, the compound containing a sulfide contaminant is selected from a gas, oil, a hydrocarbon, and a mixture thereof. In certain embodiments that may be combined with any of the preceding embodiments, the one or more (per)chlorate-reducing bacteria contain one or more recombinant nucleic acids selected from a nucleic acid that is at least 70%, 75%, 80%, 85%, 90%, 95%, 99%, or 100% identical to perA (Daro_2584); a nucleic acid that is at least 70%, 75%, 80%, 85%, 90%, 95%, 99%, or 100% identical to perB (Daro_2583); a nucleic acid that is at least 70%, 75%, 80%, 85%, 90%, 95%, 99%, or 100% identical to perC (Daro_2582); a nucleic acid that is at least 70%, 75%, 80%, 85%, 90%, 95%, 99%, or 100% identical to perD (Daro_2581); a nucleic acid that is at least 70%, 75%, 80%, 85%, 90%, 95%, 99%, or 100% identical to cld (Daro_2580); a nucleic acid that is at least 70%, 75%, 80%, 85%, 90%, 95%, 99%, or 100% identical to moaA (Daro_2577); a nucleic acid that is at least 70%, 75%, 80%, 85%, 90%, 95%, 99%, or 100% identical to QDH (Daro_2579); a nucleic acid that is at least 70%, 75%, 80%, 85%, 90%, 95%, 99%, or 100% identical to DHC (Daro_2578); a nucleic acid that is at least 70%, 75%, 80%, 85%, 90%, 95%, 99%, or 100% identical to HK (Daro_2586); a nucleic acid that is at least 70%, 75%, 80%, 85%, 90%, 95%, 99%, or 100% identical to RR (Daro_2585); a nucleic acid that is at least 70%, 75%, 80%, 85%, 90%, 95%, 99%, or 100% identical to PAS (Daro_2587); a nucleic acid that is at least 70%, 75%, 80%, 85%, 90%, 95%, 99%, or 100% identical to S (Daro_2590); a nucleic acid that is at least 70%, 75%, 80%, 85%, 90%, 95%, 99%, or 100% identical to AS (Daro_2589); a nucleic acid that is at least 70%, 75%, 80%, 85%, 90%, 95%, 99%, or 100% identical to OR1 (Daro_2591); a nucleic acid that is at least 70%, 75%, 80%, 85%, 90%, 95%, 99%, or 100% identical to OR2 (Daro_2592); and a nucleic acid that is at least 70%, 75%, 80%, 85%, 90%, 95%, 99%, or 100% identical to OR3 (Daro_2593). In certain embodiments that may be combined with any of the preceding embodiments, the one or more (per)chlorate-reducing bacteria are selected from *Ideonella*; *Dechloromarinus*; *Dechloromarinus* strain NSS; *Dechloromonas*; *Dechloromonas* strain FL2, FL8, FL9, CKB, CL, NM, MLC33, JM, HZ, CL24plus, CL24, CC0, RCB, SIUL, and MissR; *Dechloromonas aromaticae*; *Dechloromonas hortensis*; *Magnetospirillum*; *Magnetospirillum* strain SN1, WD, DB, and VDY; *Azospirillum*; *Azospirillum* strain TTI; *Azospira*; *Azospira* strain AH, Iso1, Iso2, SDGM, PDX, KJ, GR-1, and perclace; *Azospira suillum* strain PS; *Dechlorobacter*; *Dechlorobacter hydrogenophilus* strain LT-1; *Propionivibrio*; *Propionivibrio* strain MP; *Wolinella*; *Wolinella succinogenes* strain HAP-1; *Moorella*; *Moorella perchloratireducens*; *Sporomusa*; *Sporomusa* strain An4; *Proteus*; *Proteus mirabilis*; *Escherichia*; *Shewanella*; *Shewanella alga*; *Shewanella alga* strain ACDC; *Shewanella oneidensis* strain MR1; *Rhodobacter*;

*Rhodobacter capsulatus; Rhodobacter sphaeroides; Alicycliphilus; Alicycliphilus denitrificans; Pseudomonas* strain PK, CFPBD, PDA, and PDB; and *Pseudomonas chloritidismutans*. In certain embodiments that may be combined with any of the preceding embodiments, the one or more (per)chlorate-reducing bacteria are *Dechloromonas aromaticae*. In certain embodiments that may be combined with any of the preceding embodiments, the one or more (per)chlorate-reducing bacteria are *Dechloromarinus* strain NSS.

Other aspects of the present disclosure relate to a host cell, containing one or more recombinant nucleic acids selected from a nucleic acid that is at least 70%, 75%, 80%, 85%, 90%, 95%, 99%, or 100% identical to perA (Daro_2584); a nucleic acid that is at least 70%, 75%, 80%, 85%, 90%, 95%, 99%, or 100% identical to perB (Daro_2583); a nucleic acid that is at least 70%, 75%, 80%, 85%, 90%, 95%, 99%, or 100% identical to perC (Daro_2582); a nucleic acid that is at least 70%, 75%, 80%, 85%, 90%, 95%, 99%, or 100% identical to perD (Daro_2581); a nucleic acid that is at least 70%, 75%, 80%, 85%, 90%, 95%, 99%, or 100% identical to cld (Daro_2580); a nucleic acid that is at least 70%, 75%, 80%, 85%, 90%, 95%, 99%, or 100% identical to moaA (Daro_2577); a nucleic acid that is at least 70%, 75%, 80%, 85%, 90%, 95%, 99%, or 100% identical to QDH (Daro_2579); a nucleic acid that is at least 70%, 75%, 80%, 85%, 90%, 95%, 99%, or 100% identical to DHC (Daro_2578); a nucleic acid that is at least 70%, 75%, 80%, 85%, 90%, 95%, 99%, or 100% identical to HK (Daro_2586); a nucleic acid that is at least 70%, 75%, 80%, 85%, 90%, 95%, 99%, or 100% identical to RR (Daro_2585); a nucleic acid that is at least 70%, 75%, 80%, 85%, 90%, 95%, 99%, or 100% identical to PAS (Daro_2587); a nucleic acid that is at least 70%, 75%, 80%, 85%, 90%, 95%, 99%, or 100% identical to S (Daro_2590); a nucleic acid that is at least 70%, 75%, 80%, 85%, 90%, 95%, 99%, or 100% identical to AS (Daro_2589); a nucleic acid that is at least 70%, 75%, 80%, 85%, 90%, 95%, 99%, or 100% identical to OR1 (Daro_2591); a nucleic acid that is at least 70%, 75%, 80%, 85%, 90%, 95%, 99%, or 100% identical to OR2 (Daro_2592); and a nucleic acid that is at least 70%, 75%, 80%, 85%, 90%, 95%, 99%, or 100% identical to OR3 (Daro_2593), where the host cell reduces (per)chlorate.

In certain embodiments, the host cell contains two nucleic acids, three nucleic acids, four nucleic acids, five nucleic acids, six nucleic acids, seven nucleic acids, eight nucleic acids, nine nucleic acids, 10 nucleic acids, 11 nucleic acids, 12 nucleic acids, 13 nucleic acids, 14 nucleic acids, 15 nucleic acids, or 16 nucleic acids selected from a nucleic acid that is at least 70%, 75%, 80%, 85%, 90%, 95%, 99%, or 100% identical to perA (Daro_2584); a nucleic acid that is at least 70%, 75%, 80%, 85%, 90%, 95%, 99%, or 100% identical to perB (Daro_2583); a nucleic acid that is at least 70%, 75%, 80%, 85%, 90%, 95%, 99%, or 100% identical to perC (Daro_2582); a nucleic acid that is at least 70%, 75%, 80%, 85%, 90%, 95%, 99%, or 100% identical to perD (Daro_2581); a nucleic acid that is at least 70%, 75%, 80%, 85%, 90%, 95%, 99%, or 100% identical to cld (Daro_2580); a nucleic acid that is at least 70%, 75%, 80%, 85%, 90%, 95%, 99%, or 100% identical to moaA (Daro_2577); a nucleic acid that is at least 70%, 75%, 80%, 85%, 90%, 95%, 99%, or 100% identical to QDH (Daro_2579); a nucleic acid that is at least 70%, 75%, 80%, 85%, 90%, 95%, 99%, or 100% identical to DHC (Daro_2578); a nucleic acid that is at least 70%, 75%, 80%, 85%, 90%, 95%, 99%, or 100% identical to HK (Daro_2586); a nucleic acid that is at least 70%, 75%, 80%, 85%, 90%, 95%, 99%, or 100% identical to RR (Daro_2585); a nucleic acid that is at least 70%, 75%, 80%, 85%, 90%, 95%, 99%, or 100% identical to PAS (Daro_2587); a nucleic acid that is at least 70%, 75%, 80%, 85%, 90%, 95%, 99%, or 100% identical to S (Daro_2590); a nucleic acid that is at least 70%, 75%, 80%, 85%, 90%, 95%, 99%, or 100% identical to AS (Daro_2589); a nucleic acid that is at least 70%, 75%, 80%, 85%, 90%, 95%, 99%, or 100% identical to OR1 (Daro_2591); a nucleic acid that is at least 70%, 75%, 80%, 85%, 90%, 95%, 99%, or 100% identical to OR2 (Daro_2592); and a nucleic acid that is at least 70%, 75%, 80%, 85%, 90%, 95%, 99%, or 100% identical to OR3 (Daro_2593). In certain embodiments that may be combined with any of the preceding embodiments, the nucleic acid is operably linked to a regulatory sequence. In certain embodiments that may be combined with any of the preceding embodiments, the host cell is a bacterial, yeast, fungal, insect, or plant cell. In certain embodiments that may be combined with any of the preceding embodiments, the host cell is selected from *Escherichia, Shewanella, Pseudomonas, Proteus, Ralstonia, Streptomyces, Staphylococcus, Lactococcus, Bacillus, Saccharomyces, Schizosaccharomyces, Yarrowia, Hansenula, Kluyveromyces, Pichia pastoris, Aspergillus, Chrysosporium, Trichoderma, Magnetospirillum, Azospirillum, Azospira, Dechlorobacter, Propionivibrio, Wolinella, Moorella, Sporomusa, Rhodobacter,* and *Alicycliphilus*.

Other aspects of the present disclosure relate to a method of reducing (per)chlorate, by: a) providing a host cell; b) transforming said host cell with a vector containing one or more recombinant nucleic acids selected from a nucleic acid that is at least 70%, 75%, 80%, 85%, 90%, 95%, 99%, or 100% identical to perA (Daro_2584); a nucleic acid that is at least 70%, 75%, 80%, 85%, 90%, 95%, 99%, or 100% identical to perB (Daro_2583); a nucleic acid that is at least 70%, 75%, 80%, 85%, 90%, 95%, 99%, or 100% identical to perC (Daro_2582); a nucleic acid that is at least 70%, 75%, 80%, 85%, 90%, 95%, 99%, or 100% identical to perD (Daro_2581); a nucleic acid that is at least 70%, 75%, 80%, 85%, 90%, 95%, 99%, or 100% identical to cld (Daro_2580); a nucleic acid that is at least 70%, 75%, 80%, 85%, 90%, 95%, 99%, or 100% identical to moaA (Daro_2577); a nucleic acid that is at least 70%, 75%, 80%, 85%, 90%, 95%, 99%, or 100% identical to QDH (Daro_2579); a nucleic acid that is at least 70%, 75%, 80%, 85%, 90%, 95%, 99%, or 100% identical to DHC (Daro_2578); a nucleic acid that is at least 70%, 75%, 80%, 85%, 90%, 95%, 99%, or 100% identical to HK (Daro_2586); a nucleic acid that is at least 70%, 75%, 80%, 85%, 90%, 95%, 99%, or 100% identical to RR (Daro_2585); a nucleic acid that is at least 70%, 75%, 80%, 85%, 90%, 95%, 99%, or 100% identical to PAS (Daro_2587); a nucleic acid that is at least 70%, 75%, 80%, 85%, 90%, 95%, 99%, or 100% identical to S (Daro_2590); a nucleic acid that is at least 70%, 75%, 80%, 85%, 90%, 95%, 99%, or 100% identical to AS (Daro_2589); a nucleic acid that is at least 70%, 75%, 80%, 85%, 90%, 95%, 99%, or 100% identical to OR1 (Daro_2591); a nucleic acid that is at least 70%, 75%, 80%, 85%, 90%, 95%, 99%, or 100% identical to OR2 (Daro_2592); and a nucleic acid that is at least 70%, 75%, 80%, 85%, 90%, 95%, 99%, or 100% identical to OR3 (Daro_2593); and c) culturing the transformed host cell under suitable conditions to express the one or more recombinant nucleic acids, where expression of the one or more recombinant nucleic acid is sufficient for the host cell to reduce (per)chlorate.

In certain embodiments, the host cell contains two nucleic acids, three nucleic acids, four nucleic acids, five nucleic acids, six nucleic acids, seven nucleic acids, eight nucleic acids, nine nucleic acids, 10 nucleic acids, 11 nucleic acids, 12 nucleic acids, 13 nucleic acids, 14 nucleic acids, 15 nucleic acids, or 16 nucleic acids selected from a nucleic acid that is at least 70%, 75%, 80%, 85%, 90%, 95%, 99%, or 100% identical to perA (Daro_2584); a nucleic acid that is at least 70%, 75%, 80%, 85%, 90%, 95%, 99%, or 100% identical to perB (Daro_2583); a nucleic acid that is at least 70%, 75%, 80%, 85%, 90%, 95%, 99%, or 100% identical to perC (Daro_2582); a nucleic acid that is at least 70%, 75%, 80%, 85%, 90%, 95%, 99%, or 100% identical to perD (Daro_2581); a nucleic acid that is at least 70%, 75%, 80%, 85%, 90%, 95%, 99%, or 100% identical to cld (Daro_2580); a nucleic acid that is at least 70%, 75%, 80%, 85%, 90%, 95%, 99%, or 100% identical to moaA (Daro_2577); a nucleic acid that is at least 70%, 75%, 80%, 85%, 90%, 95%, 99%, or 100% identical to QDH (Daro_2579); a nucleic acid that is at least 70%, 75%, 80%, 85%, 90%, 95%, 99%, or 100% identical to DHC (Daro_2578); a nucleic acid that is at least 70%, 75%, 80%, 85%, 90%, 95%, 99%, or 100% identical to HK (Daro_2586); a nucleic acid that is at least 70%, 75%, 80%, 85%, 90%, 95%, 99%, or 100% identical to RR (Daro_2585); a nucleic acid that is at least 70%, 75%, 80%, 85%, 90%, 95%, 99%, or 100% identical to PAS (Daro_2587); a nucleic acid that is at least 70%, 75%, 80%, 85%, 90%, 95%, 99%, or 100% identical to S (Daro_2590); a nucleic acid that is at least 70%, 75%, 80%, 85%, 90%, 95%, 99%, or 100% identical to AS (Daro_2589); a nucleic acid that is at least 70%, 75%, 80%, 85%, 90%, 95%, 99%, or 100% identical to OR1 (Daro_2591); a nucleic acid that is at least 70%, 75%, 80%, 85%, 90%, 95%, 99%, or 100% identical to OR2 (Daro_2592); and a nucleic acid that is at least 70%, 75%, 80%, 85%, 90%, 95%, 99%, or 100% identical to OR3 (Daro_2593).

BRIEF DESCRIPTION OF THE DRAWINGS

FIG. 8A and FIG. 8B show the phylogenetic diversity of dissimilatory (per)chlorate-reducing bacteria (DPRB).

DETAILED DESCRIPTION

Figure 1:
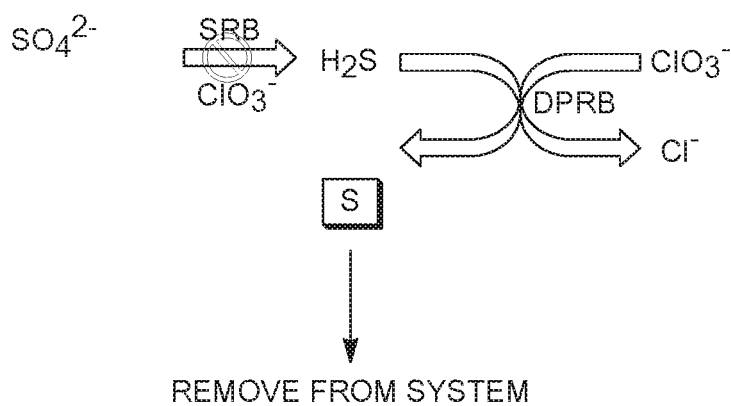
FIG. 1 shows a schematic of redox reactions occurring in a system containing sulfate-reducing bacteria (SRB) and dissimilatory (per)chlorate-reducing bacteria (DPRB) in the presence of sulfate and chlorate ions. SRB reduced sulfate ions ($SO_4^{2-}$) to produce hydrogen sulfide ($H_2S$). The presence of chlorate ions ($ClO_3^-$) can inhibit the formation of $H_2S$ by inhibiting the sulfate-reducing activity of SRB. Without wishing to be bound by theory, it is believed that the inhibitory effect of the chlorate ions is due to inhibition of one or a combination of sulfate uptake by the SRB, inhibition of the ATP-sulfurylase enzyme in SRB, or inhibition of the APS-reductase enzyme in SRB, which are all required for efficient reduction of $SO_4$ by SRB. Additionally, in the presence of chlorate ions, DPRB can oxidize the $H_2S$ to elemental sulfur coupled with reduction of $ClO_3^-$ to chloride ions ($Cl^-$). The produced sulfur can then be removed from the system.

The following description sets forth exemplary methods, parameters and the like. It should be recognized, however, that such description is not intended as a limitation on the scope of the present disclosure but is instead provided as a description of exemplary embodiments.

The present disclosure relates to methods and compositions for decreasing the amount of one or more sulfide-containing compounds in oil-containing systems by using (per)chlorate-reducing bacteria, which oxidize sulfide-containing compounds, e.g., $H_2S$, to elemental sulfur.

The present disclosure provides a method of decreasing the amount of one or more sulfide-containing compounds in a system including sulfate-reducing bacteria and (per)chlorate-reducing bacteria by adding to the system including sulfate-reducing bacteria and (per)chlorate-reducing bacteria, a composition containing chlorine oxyanions, or compounds which yield chlorine oxyanions upon addition to the system, at a concentration sufficient to stimulate (per)chlorate-reducing activity of the (per)chlorate-reducing bacteria, thereby decreasing the amount of the one or more sulfide-containing compounds in the system.

The present disclosure also provides a method of inhibiting sulfidogenesis and/or $H_2SO_4$ production in a system including sulfate-reducing bacteria by adding to the system including sulfate-reducing bacteria, a composition containing chlorine oxyanions, or compounds which yield chlorine oxyanions upon addition to the system, at a concentration sufficient to inhibit sulfate-reducing activity of the sulfate-reducing bacteria, thereby inhibiting sulfidogenesis and/or $H_2SO_4$ production in the system.

The present disclosure also provides a method of decreasing the amount of one or more sulfide-containing compounds in a system including sulfate-reducing bacteria by adding to the system including sulfate-reducing bacteria, (a) (per)chlorate-reducing bacteria and (b) chlorine oxyanions, or compounds which yield the chlorine oxyanions upon addition to the system, at a concentration sufficient to stimulate (per)chlorate-reducing activity of the (per)chlorate-reducing bacteria, thereby decreasing the amount of the one or more sulfide-containing compounds in the system. Without wishing to be bound by theory, it is believed that chlorine oxyanions (e.g., hypochlorite, chlorite, and chlorine dioxide) may also chemically react with sulfide in the sulfide-containing compound to produce sulfur.

Additionally, the present disclosure provides a system for refining a compound containing a sulfide contaminant, a chemical plant for producing a compound containing a sulfide contaminant, and a wastewater treatment plant for treating wastewater containing a sulfide contaminant, where the system includes a container that includes (per)chlorate-reducing bacteria and a compound containing a sulfide contaminant or wastewater containing a sulfide contaminant, where the system does not include a sulfide scrubber. The present disclosure also provides a container for storing a containing a sulfide contaminant, including (per)chlorate-reducing bacteria and a compound containing a sulfide contaminant I. Exemplary Systems Treated The disclosed methods can be used to treat any system where sulfate-reducing bacteria (SRB) are causing, have caused, or have the potential to cause generation of sulfide-containing compounds such as hydrogen sulfide ($H_2S$). Examples include aqueous environments such as pits or water-containment ponds and all marine environments. Additionally, the disclosed methods can be used to treat any system containing sulfide-containing compounds such as $H_2S$. Examples include oil refineries, $CO_2$ storage wells, chemical plants, desalination plants, and wastewater treatment plants.

Examples of systems in the present disclosure include ones in the field of oil recovery. The injection of water is a commonplace practice to increase oil production beyond primary production yields by maintaining reservoir pressure and sweeping oil from the injection wells towards the production wells. If seawater is used as the water source, oil souring often occurs as the seawater contains SRB and conditions conducive to the activity of SRB are created within the reservoir matrix. SRB are found in seawater, as they are indigenous to all marine environments.

Further examples of suitable systems include oil reservoirs, oil-water separators, wellheads, oil storage tanks, oil pipelines, a gas pipeline or a gas supply line, natural gas reservoir, cooling water tower, coal slurry pipelines, and other tanks or equipment that may contain SRB. In some embodiments, the system is the near-well environment of the oil reservoir. In other embodiments, the system is the environment deeper in the reservoir.

Another exemplary system includes $CO_2$ storage wells. Sulfide and oxygen present in the storage wells can stimulate microbial $H_2SO_4$ production in the wells in addition to the sulfidic sour gas. This can lead to extensive metal corrosion and concrete corrosion of the wells.

In some embodiments, the system is a processing plant that utilizes sulfide-containing compounds or compounds that produce sulfides as a byproduct. Examples of such compounds include, oil, gas, and hydrocarbons. Examples of processing plants include refineries, gas-liquid separators, and chemical plants.

In some embodiments, the system is waste waters bearing sulfur or its oxyanions from various industries. In preferred embodiments, the system is wastewater effluent from a pulp or paper mill. In other embodiments, the system is wastewater effluent from a tannery. In other embodiments, the system is wastewater effluent from a textile mill.

II. Sulfate-Reducing Bacteria (SRB)

Certain aspects of the present disclosure relate to inhibiting sulfate-reduction by (dissimilatory) sulfate-reducing bacteria (SRB). As used herein, the terms "(dissimilatory) sulfate-reducing bacteria (SRB)," "dissimilatory sulfate-reducing bacteria," "sulfate-reducing bacteria," and "SRB," are used interchangeably and refer to microorganisms that are capable of reducing sulfur or its oxyanions to sulfide ions (FIG. 1).

Dissimilatory sulfate-reducing bacteria (SRB) of the present disclosure may reduce sulfate in large amounts to obtain energy and expel the resulting sulfide as waste. Additionally, SRB of the present disclosure may utilize sulfate as the terminal electron acceptor of their electron transport chain. Typically, SRB are capable of reducing other oxidized inorganic sulfur compounds, including, without limitation, sulfite, thiosulfate, and elemental sulfur, which may be reduced to sulfide as hydrogen sulfide.

Dissimilatory sulfate-reducing bacteria (SRB) of the present disclosure are commonly found in sulfate rich environments, such as seawater, sediment, and water rich in decaying organic material. Thus, SRB are common in typical floodwater utilized in oil reservoirs, and are the major cause of sulfide production in oil reservoir souring (Vance and Thrasher, *Petroleum Microbiology*, eds B. Ollivier & M. Magot, ASM Press, 2005).

Dissimilatory sulfate-reducing bacteria (SRB) of the present disclosure include, without limitation, bacteria from both the Archaea and Bacteria domains. Examples of SRB also include, without limitation, members of the δ sub-group of Proteobacteria, such as *Desulfobacterales, Desulfovibrionales*, and *Syntrophobacterales*. In some embodiments, the SRB are from the species *Desulfovibrio* and *Desulfuromonas*.

III. (Dissimilatory) (Per)Chlorate-Reducing Bacteria (DPRB)

Other aspects of the present disclosure relate to (dissimilatory) (per)chlorate-reducing bacteria (DPRB), and their use in decreasing the amount of one or more sulfide-containing compounds, and inhibiting SRB-mediated sulfate reduction. As used herein, the terms "(dissimilatory) (per)

chlorate-reducing bacteria (DPRB)," "(dissimilatory) (per) chlorate-reducing bacteria," "dissimilatory (per)chlorate-reducing bacteria," and "DPRB" may be used interchangeably and refer to microorganisms that have perchlorate- and/or chlorate-reducing activity that allow the microorganisms to metabolize chlorine oxyanions into innocuous chloride ions (FIG. 1). Advantageously, the (per)chlorate-reducing activity of DPRB of the present disclosure can be coupled to sulfide oxidation to reduce and/or eliminate SRB-produced sulfide contaminations in systems of the present disclosure, such as oil reservoirs.

Figure 2:
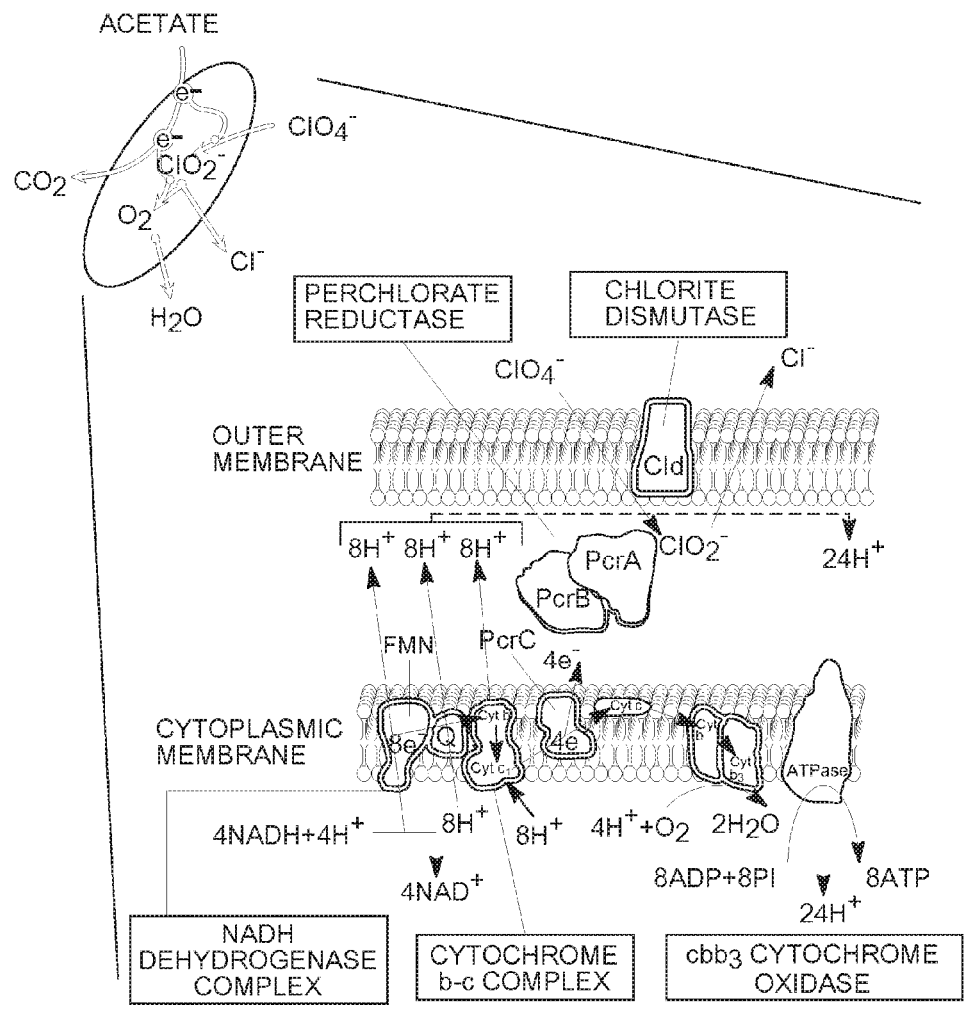
FIG. 2 shows a model of the (per)chlorate reduction pathway in dissimilatory (per)chlorate-reducing bacteria (DPRB).

Dissimilatory (per)chlorate-reducing bacteria (DPRB) of the present disclosure contain the (per)chlorate reduction pathway described in FIG. 2. In particular, DPRB of the present disclosure express at least one perchlorate reductase and at least one chlorite dismutase.

Additionally, DPRB of the present disclosure may express one or more of the following gene clusters in total or in part: perABCD (encoding components/accessory genes of perchlorate reductase), crABC (encoding chlorate reductase subunits), cld (encoding chlorite dismutase), cbb3 (encoding cytochrome oxidase), moaA (encoding molybdopterin biosynthesis protein A), QDH (encoding a membrane-associated tetraheme c-type cytochrome with quinol dehydrogenase activity), DHC (encoding a diheme c-type cytochrome), HK (encoding a histidine kinase), RR (encoding a response regulator), PAS (encoding a PAS domain sensor), S (encoding a sigma factor), AS (encoding an anti-sigma factor), and OR (encoding an oxidoreductase component). Further, DPRB of the present disclosure may also contain one or more genes encoding assimilatory nitrate reductases or dissimilatory nitrate reductases.

Moreover, DPRB of the present disclosure can also exhibit a broad range of metabolic capabilities including, without limitation, the oxidation of hydrogen, simple organic acids and alcohols, aliphatic and aromatic hydrocarbons, hexoses, reduced humic substances, both soluble and insoluble ferrous iron, electrically charged cathodes, and both soluble sulfide (e.g., $HS^-$) and insoluble sulfide (e.g., FeS). In some embodiments, the DPRB are facultatively anaerobic or micro-aerophilic with molecular oxygen being produced as a transient intermediate of the microbial reduction of (per)chlorate. Additionally, and without wishing to be bound by theory, it is believed that molybdenum is generally required by DPRB. However, it is unlikely that molybdenum is present in limiting concentrations in the natural environment. Accordingly, in some embodiments, the DPRB may be dependent on molybdenum for their metabolism.

Dissimilatory (per)chlorate-reducing bacteria (DPRB) of the present disclosure may be endogenous to any of the systems of the present disclosure, or may be added exogenously to any system of the present disclosure. Accordingly, in certain embodiments of the method of the present disclosure, the DPRB are endogenous to the system. In other embodiments, methods of the present disclosure include a step of adding exogenous DPRB to the system. For example, exogenous DPRB may be added to system via injection of either active whole cells or starved ultramicrobacteria. In still other embodiments, the exogenous DPRB are added at cell densities suitable to reduce or inhibit the activity of SRB.

Isolated DPRB

Any DPRB known in the art may be utilized in the compositions, systems, and methods of the present disclosure. Moreover, additional DPRB may be isolated from a broad diversity of environments including, without limitation, both pristine and contaminated soils and sediments. Examples of sediments include, without limitation, those from freshwater lakes, lagoons, farm swine lagoons, swamp lands, rivers, mine drainage, salt-water lakes, bays, seas, and oceans.

Methods for isolating DPRB are well known in the art, and include, without limitation, those disclosed herein, and those disclosed in Coates et al., *Appl Environ Microbiol.* 1999 December; 65(12):5234-41; Bruce et al., *Environ Microbiol.* 1999 August; 1(4):319-29; Achenbach et al., *Int J Syst Evol Microbiol.* 2001 March; 51(Pt 2):527-33; O'Connor and Coates, *Appl Environ Microbiol.* 2002 June; 68(6):3108-13; Bender et al., *Appl Environ Microbiol.* 2004 September; 70(9):5651-8; Thrasher et al., *Appl Environ Microbiol.* 2010 July; 76(14):4730-7; and Melnyk et al., *Appl Environ Microbiol.* 2011 October; 77(20):7401-4. For example, cultured-based methods, such as serial dilutions of environmental samples may be used; immunoprobe-based methods utilizing perchlorate reductase-specific antibodies and/or chlorite dismutase-specific antibodies may be used; and genetic probe-based methods utilizing probes that target perchlorate reductase and/or chlorite dismutase genes may be used. Examples of such isolated DPRB include those listed in FIGS. 7 and 8.

In one non-limiting example, DPRB enrichment cultures can be established by transferring a sample from the freshly collected soil or sediment into an anoxic medium under, for example, an $N_2$—$CO_2$ gas stream. An appropriate electron donor, such as acetate, and electron acceptor, such as (per) chlorate are included in the medium. As only microorganisms capable of reducing (per)chlorate will be able to grow in such medium, positive enrichment cultures can be identified on the basis of an increase in growth and consumption of (per)chlorate. Positive enrichment cultures can then be serially diluted to isolate individual strains.

Examples of suitable DPRB having chlorate-reducing activity include, without limitation, *Ideonella, Dechloromarinus, Shewanella,* and *Pseudomonas.*

Examples of suitable DPRB having perchlorate- and chlorate-reducing activity include, without limitation, *Dechloromarinus; Dechloromarinus* strain NSS; *Dechloromonas; Dechloromonas* strain FL2, FL8, FL9, CKB, CL, NM, MLC33, JM, HZ, CL24plus, CL24, CC0, RCB, SIUL, or MissR; *Dechloromonas aromaticae; Dechloromonas hortensis; Magnetospirillum; Magnetospirillum* strain SN1, WD, DB, or VDY; *Azospirillum; Azospirillum* strain TTI; *Azospira; Azospira* strain AH, Iso1, Iso2, SDGM, PDX, KJ, GR-1, or perc1ace; *Azospira suillum* strain PS; *Dechlorobacter; Dechlorobacter hydrogenophilus* strain LT-1; *Propionivibrio; Propionivibrio* strain MP; *Wolinella; Wolinella succinogenes* strain HAP-1; *Moorella; Moorella perchloratireducens; Sporomusa; Sporomusa* strain An4; *Proteus; Proteus mirabilis; Escherichia; Shewanella; Shewanella alga; Shewanella alga* strain ACDC; *Shewanella oneidensis* strain MR1; *Rhodobacter; Rhodobacter capsulatus; Rhodobacter sphaeroides; Alicycliphilus; Alicycliphilus denitrificans; Pseudomonas* strain PK, CFPBD, PDA, or PDB; and *Pseudomonas chloritidismutans.*

In certain preferred embodiments, the DPRB is *Dechloromonas aromaticae* or *Dechloromarinus* strain NSS.

Mutant and Variant DPRB

Dissimilatory (per)chlorate-reducing bacteria (DPRB) of the present disclosure also include mutants and variants of isolated DPRB strains (parental strains), which retain (per) chlorate-reducing activity. To obtain such mutants, the parental strain may be treated with a chemical such as N-methyl-N'-nitro-N-nitrosoguanidine, ethylmethanesulfone, or by irradiation using gamma, x-ray, or UV-irradiation, or by other means well known to those practiced in the art. Additionally, active enzymes isolated from DPRB and involved in (per)chlorate-reducing activity can be used for decreasing the amount of one or more sulfide-containing compounds in systems. Examples of enzymes include, without limitation, chlorate reductase subunits, perchlorate reductase subunits, chlorite dismutases, and cytochrome oxidases.

The term "mutant of a strain" as used herein refers to a variant of the parental strain. The parental strain is defined herein as the original isolated strain prior to mutagenesis. Mutagenesis may be accomplished by any method known in the art. Examples include, without limitation, homologous recombination, chemical mutagenesis, radiation mutagenesis, and insertional mutagenesis.

The term "variant of a strain" can be identified as having a genome that hybridizes under conditions of high stringency to the genome of the parental strain. "Hybridization" refers to a reaction in which a genome reacts to form a complex with another genome that is stabilized via hydrogen bonding between the bases of the nucleotide residues that make up the genomes. The hydrogen bonding may occur by Watson-Crick base pairing, Hoogstein binding, or in any other sequence-specific manner. The complex may contain two strands forming a duplex structure, three or more strands forming a multi-stranded complex, a single self-hybridizing strand, or any combination of these. Hybridization reactions can be performed under conditions of different "stringency." In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

In certain embodiments, DPRB added in the provided methods can be modified, e.g., by mutagenesis as described above, to stimulate (per)chlorate-reducing activity. For instance, these organisms may be modified to enhance expression of endogenous genes which may positively regulate the pathway involved in (per)chlorate-reduction. One way of achieving this enhancement is to provide additional exogenous copies of such positive regulator genes. Similarly, negative regulators of the pathway, which are endogenous to the cell, may be removed.

Recombinant DPRB

Dissimilatory (per)chlorate-reducing bacteria (DPRB) of the present disclosure of the present disclosure may further include microorganisms that do not naturally exhibit (per) chlorate-reducing activity, but where (per)chlorate-reducing activity has been introduced into the microorganism by any recombinant means known in the art. For example, the microorganism may be transformed with one or more of the perA, perB, perC, perD, cld, moaA, QDH, DHC, HK, RR, PAS, S, AS, OR1, OR2, OR3 genes, or homologs thereof. These genes are identified by the National Center for Biotechnology Information (NCBI) Gene ID numbers listed in Table 1.

TABLE 1

| Gene Name | NCBI Gene ID | Origin |
| --- | --- | --- |
| pcrA | Daro_2584 | Dechloromonas aromaticae strain RCB |
| pcrB | Daro_2583 | Dechloromonas aromaticae strain RCB |
| pcrC | Daro_2582 | Dechloromonas aromaticae strain RCB |
| pcrD | Daro_2581 | Dechloromonas aromaticae strain RCB |
| cld | Daro_2580 | Dechloromonas aromaticae strain RCB |

TABLE 1-continued

| Gene Name | NCBI Gene ID | Origin |
| --- | --- | --- |
| moaA | Daro_2577 | Dechloromonas aromaticae strain RCB |
| QDH | Daro_2579 | Dechloromonas aromaticae strain RCB |
| DHC | Daro_2578 | Dechloromonas aromaticae strain RCB |
| HK | Daro_2586 | Dechloromonas aromaticae strain RCB |
| RR | Daro_2585 | Dechloromonas aromaticae strain RCB |
| PAS | Daro_2587 | Dechloromonas aromaticae strain RCB |
| S | Daro_2590 | Dechloromonas aromaticae strain RCB |
| AS | Daro_2589 | Dechloromonas aromaticae strain RCB |
| OR1 | Daro_2591 | Dechloromonas aromaticae strain RCB |
| OR2 | Daro_2592 | Dechloromonas aromaticae strain RCB |
| OR3 | Daro_2593 | Dechloromonas aromaticae strain RCB |

DPRB-Mediated Sulfide Oxidation

In certain embodiments, DPRB of the present disclosure can inhibit microbial sulfate-reduction based on thermodynamic preferences, i.e., by competing with SRB for electron donors such as lactate or hydrocarbons, which the DPRB then subsequently use to reduce chlorine oxyanions.

The DPRB employed in the methods of the present disclosure can utilize sulfide-containing compounds, such as $H_2S$, as electron donors to produce elemental sulfur (FIG. 1).

In preferred embodiments, the disclosed methods further include a step of removing from the system, the elemental sulfur produced by the DPRB. Examples of methods of removing sulfur include, without limitation, filtration, centrifugation, and settlement ponds. Additionally, the elemental sulfur may also be used to alter the hydrology in an oil reservoir and improve sweep efficiency.

IV. Nucleic Acid Sequences Encoding DPRB Enzymes

Certain aspects of the present disclosure relate to DPRB genes encoding polypeptides involved in (per)chlorate-reduction. Accordingly, the present disclosure provides recombinant nucleic acid sequences encoding the DPRB genes perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), OR3 (Daro_2593), subsequences thereof, or homologous sequences thereof. The disclosure also provides for nucleic acid sequences having at least about 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to the nucleic acid sequences encoding perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593), where the nucleic acid sequences encode polypeptides that retain (per)chlorate-reducing activities or functions.

The recombinant nucleic acids may be synthesized, isolated, or manipulated using standard molecular biology techniques such as those described in Sambrook, J. et al. 2000. Molecular Cloning: A Laboratory Manual (Third Edition). Techniques may include cloning, expression of cDNA libraries, and amplification of mRNA or genomic DNA.

In certain embodiments, the recombinant nucleic acids of the present disclosure may be optimized for improved activity or function. As used herein, "optimized" refers to the gene encoding a polypeptide having an altered biological activity or function, such as by the genetic alteration of the gene such that the encoded polypeptide has improved functional characteristics in relation to the wild-type polypeptide. An exemplary optimized gene may encode a polypeptide containing one or more alterations or mutations in its amino acid coding sequence (e.g., point mutations, deletions, addition of heterologous sequences) that facilitate improved expression and/or stability, allow regulation of polypeptide activity or function in relation to a desired substrate (e.g., inducible or repressible activity), modulate the localization of the polypeptide within a cell (e.g., intracellular localization, extracellular secretion), and/or affect the polypeptide's overall level of activity in relation to a desired substrate (e.g., reduce or increase enzymatic activity). In this manner, a polypeptide may be optimized with or without altering its wild-type amino acid sequence or original chemical structure. Optimized genes may be obtained, for example, by direct mutagenesis or by natural selection for a desired phenotype, according to techniques known in the art.

In certain embodiments, the DPRB can have optimized gene or polypeptide sequences involved in (per)chlorate-reduction, which include a nucleic acid coding sequence or amino acid sequence that is 50% to 99% identical to the nucleic acid or amino acid sequence of the reference (e.g., wild-type) gene or polypeptide. In certain embodiments, the optimized polypeptide may have about 1, 2, 3, 4, 5, 6, 7, 8, 9, 10, 20, 30, 40, 50, 100 (including all integers and decimal points in between, e.g., 1.2, 1.3, 1.4, 1.5, 5.5, 5.6, 5.7, 60, 70, etc.), or more times the biological activity or function of a reference polypeptide.

The recombinant nucleic acids of the present disclosure, or subsequences thereof, may be incorporated into a cloning vehicle containing an expression cassette or vector. The cloning vehicle can be a viral vector, a plasmid, a phage, a phagemid, a cosmid, a fosmid, a bacteriophage, or an artificial chromosome. The viral vector can comprise an adenovirus vector, a retroviral vector, or an adeno-associated viral vector. The cloning vehicle can contain a bacterial artificial chromosome (BAC), a plasmid, a bacteriophage P1-derived vector (PAC), a yeast artificial chromosome (YAC), or a mammalian artificial chromosome (MAC).

The nucleic acids may be operably linked to a promoter. The promoter can be a viral, bacterial, mammalian or plant promoter. The promoter can be a constitutive promoter, an inducible promoter, a tissue-specific promoter, or an environmentally regulated or a developmentally regulated promoter.

The present disclosure further provides transformed host cells including the recombinant nucleic acid having a nucleic acid sequence encoding perA (Daro_2584); alone or in combination with one or more of the recombinant nucleic acid having nucleic acid sequences encoding perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure also provides for host cells including the recombinant nucleic acid having a nucleic acid sequence encoding perB (Daro_2583); alone or in combination with one or more of the recombinant nucleic acid having nucleic acid sequences encoding perA (Daro_2584), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure also provides for host cells including the recombinant nucleic acid having a nucleic acid sequence encoding perC (Daro_2582); alone or in combination with one or more of the recombinant nucleic acid having nucleic acid sequences encoding perA (Daro_2584), perB (Daro_2583), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure also provides for host cells including the recombinant nucleic acid having a nucleic acid sequence encoding perD (Daro_2581); alone or in combination with one or more of the recombinant nucleic acid having nucleic acid sequences encoding perA (Daro_2584), perB (Daro_2583), perC (Daro_2582), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure also provides for host cells including the recombinant nucleic acid having a nucleic acid sequence encoding cld (Daro_2580); alone or in combination with one or more of the recombinant nucleic acid having nucleic acid sequences encoding perA (Daro_2584), perB (Daro_2583), perC (Daro_2582), perD (Daro_2581), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure also provides for host cells including the recombinant nucleic acid having a nucleic acid sequence encoding moaA (Daro_2577); alone or in combination with one or more of the recombinant nucleic acid having nucleic acid sequences encoding perA (Daro_2584), perB (Daro_2583), perC (Daro_2582), perD (Daro_2581), cld (Daro_2580), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure also provides for host cells including the recombinant nucleic acid having a nucleic acid sequence encoding QDH (Daro_2579); alone or in combination with one or more of the recombinant nucleic acid having nucleic acid sequences encoding perA (Daro_2584), perB (Daro_2583), perC (Daro_2582), perD (Daro_2581), cld (Daro_2580), moaA (Daro_2577), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure also provides for host cells including the recombinant nucleic acid having a nucleic acid sequence encoding DHC (Daro_2578); alone or in combination with one or more of the recombinant nucleic acid having nucleic acid sequences encoding perA (Daro_2584), perB (Daro_2583), perC (Daro_2582), perD (Daro_2581), cld (Daro_2580), moaA (Daro_2577), QDH (Daro_2579), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure also provides for host cells including the recombinant nucleic acid having a nucleic acid sequence encoding HK (Daro_2586); alone or in combination with one or more of the recombinant nucleic acid having nucleic acid sequences encoding perA (Daro_2584), perB (Daro_2583), perC (Daro_2582), perD (Daro_2581), cld (Daro_2580), moaA (Daro_2577), QDH (Daro_2579), DHC (Daro_2578), RR (Daro_2585), PAS (Daro_2587), S (Daro_2590), AS (Daro_2589), OR1 (Daro_2591), OR2 (Daro_2592), and OR3 (Daro_2593). The present disclosure also provides for host cells including the recombinant nucleic acid having a nucleic acid sequence encoding RR (Daro_2585); alone or in combination with one or more of the recombinant nucleic acid having nucleic acid sequences encoding perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), PAS (Daro_2587), S (Daro_2590), AS (Daro_2589), OR1 (Daro_2591), OR2 (Daro_2592), and OR3 (Daro_2593). The present disclosure also provides for host cells including the recombinant nucleic acid having a nucleic acid sequence encoding PAS (Daro_2587); alone or in combination with one or more of the recombinant nucleic acid having nucleic acid sequences encoding perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), S (Daro_2590), AS (Daro_2589), OR1 (Daro_2591), OR2 (Daro_2592), and OR3 (Daro_2593). The present disclosure also provides for host cells including the recombinant nucleic acid having a nucleic acid sequence encoding S (Daro_2590); alone or in combination with one or more of the recombinant nucleic acid having nucleic acid sequences encoding perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), AS (Daro_2589), OR1 (Daro_2591), OR2 (Daro_2592), and OR3 (Daro_2593). The present disclosure also provides for host cells including the recombinant nucleic acid having a nucleic acid sequence encoding AS (Daro_2589); alone or in combination with one or more of the recombinant nucleic acid having nucleic acid sequences encoding perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), OR1 (Daro_2591), OR2 (Daro_2592), and OR3 (Daro_2593). The present disclosure also provides for host cells including the recombinant nucleic acid having a nucleic acid sequence encoding OR1 (Daro_2591); alone or in combination with one or more of the recombinant nucleic acid having nucleic acid sequences encoding perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR2 (Daro_2592), and OR3 (Daro_2593). The present disclosure also provides for host cells including the recombinant nucleic acid having a nucleic acid sequence encoding OR2 (Daro_2592); alone or in combination with one or more of the recombinant nucleic acid having nucleic acid sequences encoding perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), and OR3 (Daro_2593). The present disclosure also provides for host cells including the recombinant nucleic acid having a nucleic acid sequence encoding OR3 (Daro_2593); alone or in combination with one or more of the recombinant nucleic acid having nucleic acid sequences encoding perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), and OR2 (Daro_2592).

In certain embodiments, the unmodified host cell does not have (per)chlorate-reducing activity. However, upon transformation with one or more recombinant nucleic acids of the present disclosure, the transformed host cell has (per)chlorate-reducing activity.

The present disclosure also provides for host cells including two or more, three or more, four or more, five or more, six or more, seven or more, eight or more, nine or more, 10 or more, 11 or more, 12 or more, 13 or more, 14 or more, 15 or more, or all 16 of the recombinant nucleic acids containing nucleic acid sequences encoding perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593).

In certain embodiments, host cells that do not normally reduce (per)chlorate, can be made to reduce (per)chlorate by transforming the cell with a vector containing one or more, two or more, three or more, four or more, five or more, six or more, seven or more, eight or more, nine or more, 10 or more, 11 or more, 12 or more, 13 or more, 14 or more, 15 or more, or all 16 of the recombinant nucleic acids containing nucleic acid sequences encoding perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593); and culturing the transformed cell under suitable conditions to express the one or more, two or more, three or more, four or more, five or more, six or more, seven or more, eight or more, nine or more, 10 or more, 11 or more, 12 or more, 13 or more, 14 or more, 15 or more, or all 16 recombinant nucleic acids, where expression of the nucleic acids is sufficient for the host cell to reduce (per)chlorate.

The transformed host cell can be, without limitation, a bacterial, yeast, fungal, insect, or plant cell. In certain embodiments, the transformed host cell is selected from *Escherichia, Shewanella, Pseudomonas, Proteus, Ralstonia, Streptomyces, Staphylococcus, Lactococcus, Bacillus, Saccharomyces, Schizosaccharomyces, Yarrowia, Hansenula, Kluyveromyces, Pichia pastoris, Aspergillus, Chrysosporium, Trichoderma, Magnetospirillum, Azospirillum, Azospira, Dechlorobacter, Propionivibrio, Wolinella, Moorella, Sporomusa, Rhodobacter*, and *Alicycliphilus*.

V. Amino Acid Sequences Encoding DPRB Enzymes

The disclosure also provides for the polypeptide encoded by the DPRB genes perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), OR3 (Daro_2593), or subsequences thereof. The polypeptides of the present disclosure may contain an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity/sequence similarity to the amino acid sequence encoded by the DPRB genes perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593), where the encoded polypeptides retain (per)chlorate-reducing activities or functions.

The polypeptides of the present disclosure can be expressed in and purified from their native host. The polypeptides may also be expressed in and purified from transgenic expression systems. Transgenic expression systems can be prokaryotic or eukaryotic. Transgenic host cells may include yeast and E. coli. Transgenic host cells may secrete the polypeptide out of the host cell. In certain embodiments, the isolated or recombinant polypeptide lacks a signal sequence.

The present disclosure also provides transformed host cells expressing the polypeptide encoded by the amino acid sequence of perA (Daro_2584); alone or in combination with one or more of the polypeptides encoded by the amine acid sequences of perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure provides transformed host cells expressing the polypeptide encoded by the amino acid sequence of perB (Daro_2583); alone or in combination with one or more of the polypeptides encoded by the amine acid sequences of perA (Daro_2584), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure provides transformed host cells expressing the polypeptide encoded by the amino acid sequence of perC (Daro_2582); alone or in combination with one or more of the polypeptides encoded by the amine acid sequences of perA (Daro_2584), perB (Daro_2583), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure provides transformed host cells expressing the polypeptide encoded by the amino acid sequence of perD (Daro_2581); alone or in combination with one or more of the polypeptides encoded by the amine acid sequences of perA (Daro_2584), perB (Daro_2583), perC (Daro_2582), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure provides transformed host cells expressing the polypeptide encoded by the amino acid sequence of cld (Daro_2580); alone or in combination with one or more of the polypeptides encoded by the amine acid sequences of perA (Daro_2584), perB (Daro_2583), perC (Daro_2582), perD (Daro_2581), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure provides transformed host cells expressing the polypeptide encoded by the amino acid sequence of moaA (Daro_2577); alone or in combination with one or more of the polypeptides encoded by the amine acid sequences of perA (Daro_2584), perB (Daro_2583), perC (Daro_2582), perD (Daro_2581), cld (Daro_2580), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure provides transformed host cells expressing the polypeptide encoded by the amino acid sequence of QDH (Daro_2579); alone or in combination with one or more of the polypeptides encoded by the amine acid sequences of perA (Daro_2584), perB (Daro_2583), perC (Daro_2582), perD (Daro_2581), cld (Daro_2580), moaA (Daro_2577), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure provides transformed host cells expressing the polypeptide encoded by the amino acid sequence of DHC (Daro_2578); alone or in combination with one or more of the polypeptides encoded by the amine acid sequences of perA (Daro_2584), perB (Daro_2583), perC (Daro_2582), perD (Daro_2581), cld (Daro_2580), moaA (Daro_2577), QDH (Daro_2579), HK (Daro_2586), RR (Daro_2585), PAS (Daro_2587), S (Daro_2590), AS (Daro_2589), OR1 (Daro_2591), OR2 (Daro_2592), and OR3 (Daro_2593). The present disclosure provides transformed host cells expressing the polypeptide encoded by the amino acid sequence of HK (Daro_2586); alone or in combination with one or more of the polypeptides encoded by the amine acid sequences of perA (Daro_2584), perB (Daro_2583), perC (Daro_2582), perD (Daro_2581), cld (Daro_2580), moaA (Daro_2577), QDH (Daro_2579), DHC (Daro_2578), RR (Daro_2585), PAS (Daro_2587), S (Daro_2590), AS (Daro_2589), OR1 (Daro_2591), OR2 (Daro_2592), and OR3 (Daro_2593). The present disclosure provides transformed host cells expressing the polypeptide encoded by the amino acid sequence of RR (Daro_2585); alone or in combination with one or more of the polypeptides encoded by the amine acid sequences of perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), PAS (Daro_2587), S (Daro_2590), AS (Daro_2589), OR1 (Daro_2591), OR2 (Daro_2592), and OR3 (Daro_2593). The present disclosure provides transformed host cells expressing the polypeptide encoded by the amino acid sequence of PAS (Daro_2587); alone or in combination with one or more of the polypeptides encoded by the amine acid sequences of perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), S (Daro_2590), AS (Daro_2589), OR1 (Daro_2591), OR2 (Daro_2592), and OR3 (Daro_2593). The present disclosure provides transformed host cells expressing the polypeptide encoded by the amino acid sequence of S (Daro_2590); alone or in combination with one or more of the polypeptides encoded by the amine acid sequences of perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), AS (Daro_2589), OR1 (Daro_2591), OR2 (Daro_2592), and OR3 (Daro_2593). The present disclosure provides transformed host cells expressing the polypeptide encoded by the amino acid sequence of AS (Daro_2589); alone or in combination with one or more of the polypeptides encoded by the amine acid sequences of perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), OR1 (Daro_2591), OR2 (Daro_2592), and OR3 (Daro_2593). The present disclosure provides transformed host cells expressing the polypeptide encoded by the amino acid sequence of OR1 (Daro_2591) alone or in combination with one or more of the polypeptides encoded by the amine acid sequences of perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR2 (Daro_2592), and OR3 (Daro_2593). The present disclosure provides transformed host cells expressing the polypeptide encoded by the amino acid sequence of OR2 (Daro_2592); alone or in combination with one or more of the polypeptides encoded by the amine acid sequences of perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), and OR3 (Daro_2593). The present disclosure provides transformed host cells expressing the polypeptide encoded by the amino acid sequence of OR3 (Daro_2593); alone or in combination with one or more of the polypeptides encoded by the amine acid sequences of perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), and OR2 (Daro_2592).

In certain embodiments, the unmodified host cell does not have (per)chlorate-reducing activity. However, upon transformation, the host cell expresses the one or more polypeptides of the present disclosure, which results in the transformed host cell having (per)chlorate-reducing activity.

The present disclosure also provides for host cells including two or more, three or more, four or more, five or more, six or more, seven or more, eight or more, nine or more, 10 or more, 11 or more, 12 or more, 13 or more, 14 or more, 15 or more, or 16 of the polypeptides encoded by the nucleic acid sequences of perA (Daro_2584), perB (Daro_2583), perC (Daro_2582), perD (Daro_2581), cld (Daro_2580), moaA (Daro_2577), QDH (Daro_2579), DHC (Daro_2578), HK (Daro_2586), RR (Daro_2585), PAS (Daro_2587), S (Daro_2590), AS (Daro_2589), OR1 (Daro_2591), OR2 (Daro_2592), and OR3 (Daro_2593).

In certain embodiments, the one or more polypeptides of the present disclosure may be secreted from the transgenic host cell.

VI. Variants, Sequence Identity, and Sequence Similarity

Methods of alignment of sequences for comparison are well-known in the art. For example, the determination of percent sequence identity between any two sequences can be accomplished using a mathematical algorithm Non-limiting examples of such mathematical algorithms are the algorithm of Myers and Miller (1988) CABIOS 4:11 17; the local homology algorithm of Smith et al. (1981) Adv. Appl. Math. 2:482; the homology alignment algorithm of Needleman and Wunsch (1970) J. Mol. Biol. 48:443 453; the search-for-similarity-method of Pearson and Lipman (1988) Proc. Natl. Acad. Sci. 85:2444 2448; the algorithm of Karlin and Altschul (1990) Proc. Natl. Acad. Sci. USA 872264, modified as in Karlin and Altschul (1993) Proc. Natl. Acad. Sci. USA 90:5873 5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237 244 (1988); Higgins et al. (1989) CABIOS 5:151 153; Corpet et al. (1988) Nucleic Acids Res. 16:10881 90; Huang et al. (1992) CABIOS 8:155 65; and Pearson et al. (1994) Meth. Mol. Biol. 24:307 331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

As used herein, sequence identity or identity in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical and often differ by conservative amino acid substitutions, where amino acid residues are substituted for other amino acid residues with similar chemical properties (e.g., charge or hydrophobicity), do not change the functional properties of the molecule. When sequences differ in conservative substitutions, the percent sequence identity may be adjusted upwards to correct for the conservative nature of the substitution. Sequences that differ by such conservative substitutions are said to have sequence similarity or similarity. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

VII. Addition of Chlorine Oxyanions or Compounds Yielding Chlorine Oxyanions

The present disclosure provides methods, which include adding chlorine oxyanions or compounds yielding chlorine oxyanions to a system, to decrease the amount of sulfide-containing compounds in the system. In some embodiments, the chlorine oxyanions can be added in a batch or a continuous manner. The method of addition depends on the system being treated. For example, in embodiments where the system is a single oil well, the chlorine oxyanions can be added in a single batch injection. In other embodiment where the system is an entire oil-recovery system, the chlorine oxyanions can be added in a continuous process.

Examples of chlorine oxyanions include, without limitation, hypochlorite, chlorine dioxide, chlorite, chlorate, perchlorate, and mixtures thereof.

In embodiments where the method is used to decrease the amount of sulfide-containing compounds in an oil reservoir, the chlorine oxyanions can be added into injected water at the beginning of the flooding process. Alternatively, the chlorine oxyanions can also be added to makeup waters out in the field after souring has been observed. In other embodiments, the chlorine oxyanions can be added at the wellhead.

In further other embodiments, chlorine oxyanions are added to $CO_2$ storage wells to reduce or inhibit the formation of sour gas by SRB or sulfur oxidizing bacteria present in the storage wells. In this manner, chlorine oxyanions can protect the storage wells from the metal corrosion and concrete corrosion that may occur as the result of sour gas formation.

In the present disclosure, the chlorine oxyanions added are at a concentration sufficient to stimulate (per)chlorate-reducing activity of the DPRB. This concentration is dependent upon the parameters of the system being treated by the provided method. For example, characteristics of the system, such as its volume, surrounding pH, temperature, sulfate concentration, etc., will dictate how much chlorine oxyanions are needed to stimulate the (per)chlorate-reducing activity of the DPRB. Without wishing to be bound by theory, it is believed that a ratio of three $S^{2-}$ ions to one $ClO_3^-$ ion will completely oxidize all of the sulfide to elemental sulfur. Additionally, it is believed that this ratio changes to 4:1 with perchlorate, and 2:1 with chlorite or chlorine dioxide. Accordingly, in some embodiments, the chlorine oxyanions added are at a ratio with sulfide that is sufficient to completely oxidize the sulfide to elemental sulfur.

In embodiments where perchlorate ($ClO_4^-$) is added, the perchlorate can be added in an amount that is at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 80%, at least 85%, at least 90%, at least 95%, or at least 100% of the amount (i.e., concentration) of sulfate present in the system. Methods for determining the concentration of sulfate present in a system, such as oil reservoir, are well known in the art. In one non-limiting example, sea water, which can be used as floodwater in an oil reservoir, has a sulfate concentration of about 25 mM.

The chlorine oxyanions added to the system may be in any desired form. For example, the counter ion is not critical and accordingly any desired form of the chlorine oxyanions may be added so long as the ions perform their desired function. Examples of suitable counter ions include, without limitation, chlorine oxyanion acids and salts of sodium, potassium, magnesium, calcium, lithium, ammonium, silver, rubidium, and cesium.

Compounds, which yield chlorine oxyanions upon addition to the system, can also be used.

VIII. Addition of Other Factors

Certain aspects of the present disclosure relate to adding additional nutrients to a system of the present disclosure to stimulate (per)chlorate-reducing activity of DPRB of the present disclosure; and to adding additional anions, such as nitrite ($NO_2^-$) to further inhibit SRB present in the system.

In some embodiments, nutrients can be added to the system, which stimulate (per)chlorate-reducing activity of the DPRB. Examples of such nutrients include, without limitation, molybdenum, additional carbon sources, and/or phosphorous ions (e.g., phosphite and phosphate).

Nitrite, in small amounts, is very toxic to SRB. Accordingly, nitrite can be added in combination with (per)chlorate to inhibit SRB, thereby inhibiting sulfidogenesis. In certain embodiments, the nitrite is added at a concentration sufficient to inhibit the SRB. Generally, the nitrite can be added in combination with (per)chlorate at a (per)chlorate:nitrite ratio of at least 10:1, at least 20:1, at least 30:1, at least 40:1, at least 50:1, at least 60:1, at least 70:1, at least 80:1, at least 90:1, at least 100:1, at least 110:1, at least 120:1, at least 130:1, at least 140:1, at least 150:1, at least 160:1, at least 170:1, at least 180:1, at least 190:1, at least 200:1, or more. In certain preferred embodiments, (per)chlorate and nitrite are added in a ratio of 100:1. For example 10 mM of (per)chlorate and 100 µM of nitrite may be added to the system.

Additionally, nitrate-reducing bacteria can reduce chlorate to chlorite. Moreover, it has been shown that in pure culture that the produced chlorite can kill the nitrate-reducing bacteria. However, without wishing to be bound by theory, it is believed that in a sulfidogenic environment, such as an oil reservoir, the chlorite can inhibit SRB. Accordingly, in certain embodiments, nitrite may be added to a system of the present disclosure, such as an oil reservoir, in an amount sufficient to stimulate nitrate reduction to expand the population of nitrate-reducing bacteria in the system. Once the microbial population has been expanded, chlorine oxyanions, such as (per)chlorate, can be added to biogenically produce chlorite in an amount sufficient to inhibit SRB.

IX. Systems for Refining, Producing, or Processing Compounds Containing Sulfide Contaminants The present disclosure also provides systems for removing sulfide contaminants from sulfide-containing compounds, such as gas, oil, hydrocarbons, and wastewaters.

Sulfide-containing compounds are a common contaminant in products such as gases, oil, hydrocarbons, and wastewaters. It is common for processing plants, such as refineries, gas processing plants, chemical processing plants, and wastewater treatment plants, to employ sulfide scrubbers to remove sulfide contaminants. Scrubbers can either be physical solvents that remove sulfide by straight absorption, or they can include amines that remove sulfide through a chemical reaction. For example, amine scrubbing units utilize aqueous solutions of various alkylamines (commonly referred to simply as amines) to remove hydrogen sulfide from gases. A typical amine scrubbing unit includes an absorber unit and a regenerator unit. In the absorber, the downflowing amine solution absorbs $H_2S$ from the upflowing sour gas to produce a sweetened gas stream (i.e., an $H_2S$-free gas) as a product and an amine solution rich in the absorbed $H_2S$. The resultant "rich" amine is then routed into the regenerator (a stripper with a reboiler) to produce regenerated or "lean" amine that is recycled for reuse in the absorber. The stripped overhead gas from the regenerator is concentrated $H_2S$. This $H_2S$-rich stripped gas stream is then usually routed into a Claus process to convert it into elemental sulfur.

Advantageously, the DPRB of the present disclosure may be used to remove and/or minimize the accumulation of sulfide contaminants in processing plants, thus removing the need for such sulfide scrubbers. Additionally, the DPRB of the present disclosure completely oxidize sulfides to elemental sulfur, thus removing the need for additional processes that convert the concentrated $H_2S$-rich gas into elemental sulfur. For example, the DRPB of the present disclosure may be used in an oil refinery. The DRPB can be injected into a container, such as a tank, that contains the contaminated oil. The contaminated oil can then be incubated with the DRPB in the container as part of the refining process.

Accordingly, certain embodiments of the present disclosure provide a system for refining a compound containing a sulfide contaminant, including a container that includes (per)chlorate-reducing bacteria and a compound containing a sulfide contaminant, where the system does not contain a sulfide scrubber. As used herein a "system for refining a sulfide-containing compound" refers to any refinery known in the art. Examples of refineries include, without limitation, oil refineries and gas processing plants. Other embodiments of the present disclosure provide a chemical plant for producing a compound containing a sulfide contaminant, including a container that includes (per)chlorate-reducing bacteria and a compound containing a sulfide contaminant, where the system does not contain a sulfide scrubber. As used herein, a "chemical plant" refers to any plant known in the art that manufactures or processes chemicals. Examples of chemical plants include, without limitation, hydrocarbon processing plants and petrochemical plants. Further embodiments of the present disclosure provide a wastewater treatment plant for treating wastewater containing a sulfide contaminant, including a container that includes (per)chlorate-reducing bacteria and wastewater containing a sulfide contaminant, where the system does not contain a sulfide scrubber. Any wastewater treatment plant known in the art may be used.

In some embodiments, the container is located within or in close proximity to any of disclosed refineries or plants. In other embodiments, the container is located at a location that is geographically distinct from the refinery or plant. For example, in the case of an oil refinery, the container may be located near an oil well or oil field. Alternatively, the container may be part of a conveyance vehicle that transports the sulfide-containing compound to the refinery or plant.

In certain embodiments, the compound containing a sulfide contaminant is selected from a gas, oil, a hydrocarbon, and a mixture thereof. The sulfide contaminant may be present in any raw material or starting material that is used in the refining, treatment, or production process of any of the systems of the present disclosure. Alternatively, the sulfide contaminant may be a byproduct of the refining, treatment, or production process of any of the systems of the present disclosure. In certain embodiments, the sulfide contaminant is hydrogen sulfide. In other embodiments, the container further contains chlorine oxyanions. Preferably, the chlorine oxyanions are chlorine dioxide, chlorite, chlorate, perchlorate, or a mixture thereof. In still other embodiments, the (per)chlorate-reducing bacteria are *Dechloromonas aromaticae*. Preferably, the (per)chlorate-reducing bacteria are *Dechloromarinus* strain NSS.

In other embodiments, (per)chlorate-reducing bacteria are used to inhibit sour gas formation in $CO_2$ storage wells. In this manner, (per)chlorate-reducing bacteria can protect the storage wells from the metal corrosion and concrete corrosion that may occur as the result of sour gas formation.

Further aspects of the present disclosure also relate to a container for storing a compound containing a sulfide contaminant, that includes (per)chlorate-reducing bacteria and a compound containing a sulfide contaminant. In some embodiments, the container further contains chlorine oxyanions. Preferably, the chlorine oxyanions are chlorine dioxide, chlorite, chlorate, perchlorate, or a mixture thereof. In other embodiments, the sulfide contaminant is hydrogen sulfide. In still other embodiments, the compound containing a sulfide contaminant is selected from a gas, oil, a hydrocarbon, and a mixture thereof. In yet other embodiments, the (per)chlorate-reducing bacteria are *Dechloromonas aromaticae*. Preferably, the (per)chlorate-reducing bacteria are *Dechloromarinus* strain NSS.

EXAMPLES

Example 1—Characterization of *Dechloromarinus* Strain NSS

A chlorate-reducing organism *Dechloromarinus* strain NSS was isolated from hydrocarbon-contaminated harbor sediments collected from the Naval Station San Diego Bay, Calif. Strain NSS grew optimally at 30° C., pH 7.5, in 4% NaCl (mass per volume) salinity. However, growth was observed at up to 40° C. and a salinity of 10% NaCl (mass per volume). Phenotypic characterization revealed that in addition to chlorate, which was completely reduced to chloride, strain NSS could alternatively grow anaerobically with nitrate. Strain NSS could utilize a range of simple organic acids and alcohols as alternative electron donors. In addition, *Dechloromarinus* strain NSS also utilized Fe (II) or $H_2S$ coupled to the reduction of chlorate.

Oxidation of Sulfide to Elemental Sulfur

Cells of *Dechloromarinus* strain NSS were grown anaerobically in 1000 mL of medium containing acetate as the electron donor and chlorate as the electron acceptor. After the desired growth (i.e., mid log phase), the cells were harvested by centrifugation and washed with anoxic bicarbonate buffer (2.5 g/L) under a headspace of $N_2$—$CO_2$ (80:20; v/v). The washed cells were then resuspended in 1 mL anoxic bicarbonate buffer and sealed in a 10 mL serum vial with a thick butyl rubber stopper under a headspace of $N_2$—$CO_2$ and were used immediately for experiments. For the experiments, the cells were treated with: 1) $Na_2S$ at a final concentration of 10 mM; 2) $NaClO_3$ at a final concentration of 10 mM; or 3) $Na_2S$ and $NaClO_3$, both supplied at a final concentration of 10 mM. The cells were incubated with each treatment for a period of several weeks.

Heat-killed cells were prepared by placing a portion of the cell suspension in boiling water for 5 mM and then cooling the cells. The presence of chlorate, chloride, nitrate, nitrite, sulfate, and sulfite were determined using a Dionex DX500 ion chromatograph (Dionex Corporation, Sunnyvale, Calif.) equipped with a GP50 gradient pump, CD20 conductivity detector, ASRS-Ultra for suppressed conductivity, and PeakNet 6 controlling software. An IonPac AS9-SC 4×250 mm column was used for analysis with bicarbonate buffer containing 2 mM sodium carbonate and 0.75 mM sodium bicarbonate at a flow rate of 2 (mL min−1) as the eluent. The SRS current was set at 100 mA for all the analysis.

Figure 3A:
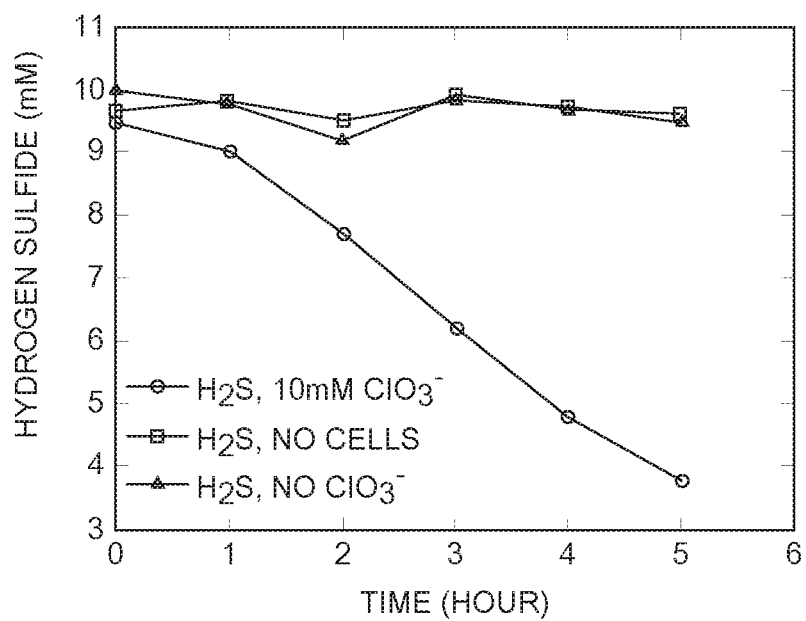
FIG. 3A shows chlorate-dependent sulfide oxidation to elemental sulfur ($S^0$) by *Dechloromarinus* strain NSS. $H_2S$ is oxidized to elemental sulfur ($S^0$). No oxyanions of sulfur (sulfite, thiosulfite, etc.) are produced even after extended incubation of several weeks.
Figure 3B:
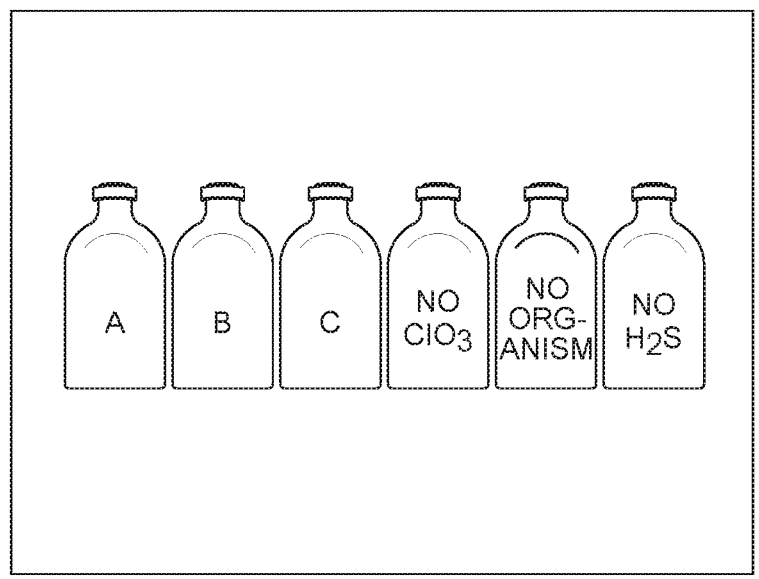
FIG. 3B shows that elemental sulfur is precipitated out of aqueous solution.

As shown in FIG. 3, the sulfide was oxidized to elemental sulfur, which precipitated out of solution. Furthermore, no sulfur oxyanions (e.g., sulfate, sulfite, etc.) were observed even after extended incubations.

Figure 4:
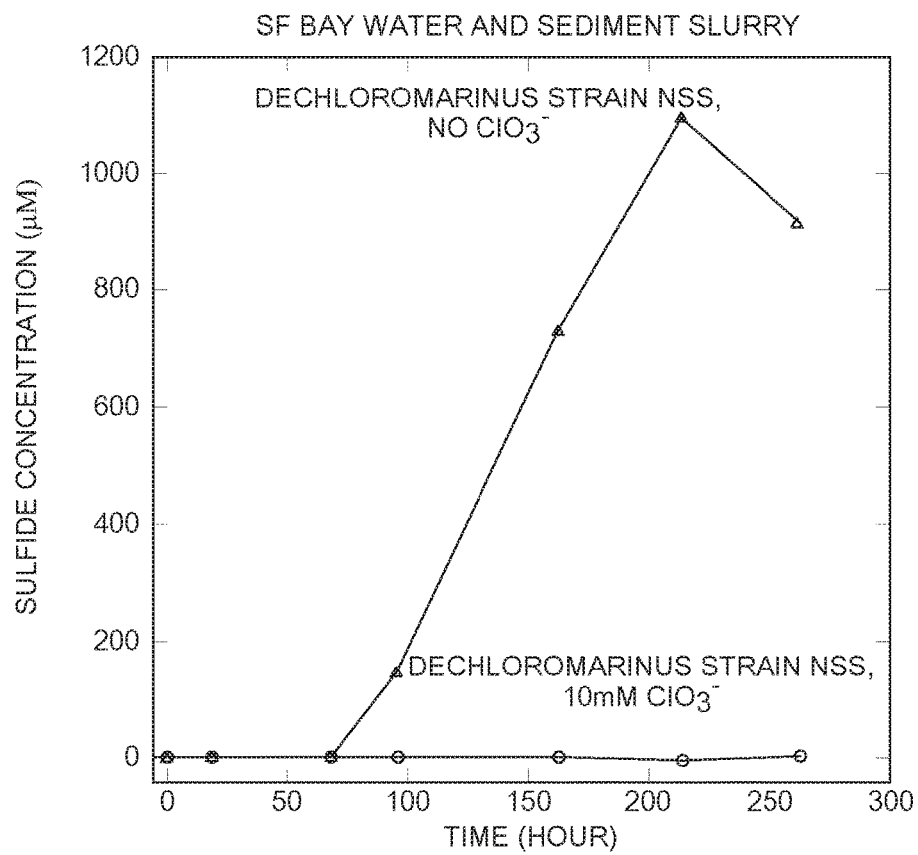
FIG. 4 shows sulfide inhibition in marine sediment slurry microcosms after extended incubation for over 250 hours after addition of chlorate and *Dechloromarinus* strain NSS. In the absence of chlorate and *Dechloromarinus* strain NSS sulfide is readily produced.

FIG. 4 shows sulfide inhibition in marine sediment slurry microcosms after extended incubation for over 250 hours after addition of chlorate and *Dechloromarinus* strain NSS. In the absence of chlorate and *Dechloromarinus* strain NSS sulfide is readily produced.

Example 2—Inhibition of Sulfate-Reducing Bacteria (SRB)

To demonstrate the inhibition of microbial sulfate reduction, active cells of the sulfate reducing species *Desulfovibrio vulgaris* were incubated with the (per)chlorate reducing species *Azospira suillum*. Twelve tubes of basal anaerobic medium containing 15 mM lactate and 15 mM sulfate were inoculated with an active culture of *D. vulgaris* and incubated for 6 hours at 30° C., until a visible increase in optical density was observed. After six hours, the tubes were further inoculated with *A. suillum* and 15 mM chlorate prior to incubation overnight at 30° C., as outlined in Table 2.

TABLE 2

| Experimental tube treatment | | | |
| --- | --- | --- | --- |
| Tube Number | D. vulgaris | A. suillum | Chlorate |
| 1-3 | Yes | Yes | Yes |
| 4-6 | Yes | No | Yes |
| 6-10 | Yes | No | No |
| 11-12 | No | Yes | Yes |

Figure 5:
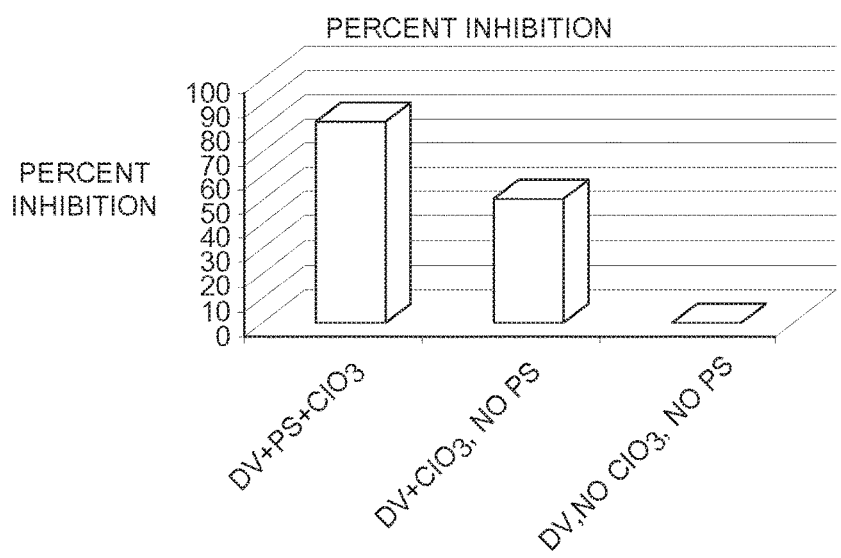
FIG. 5 shows the percent inhibition of sulfidogenesis by the SRB *D. vulgaris* (DV) after a 24-hour incubation with the (per)chlorate reducing organism *A. suillum* (PS) and/or chlorate ($ClO_3$).

The results indicated that sulfate reduction to sulfide was significantly inhibited when lactate was used as the electron donor. Additionally, after the 24-hour incubation with *A. suillum* and 15 mM chlorate, sulfide production by *D. vulgaris* was only 17% of the sulfide production seen in the control cells incubated in the absence of *A. suillum* and 15 mM chlorate (FIG. 5). It was also observed that thick cell growth was still apparent in the culture tubes of the *D. vulgaris* cells incubated with *A. suillum* and 15 mM chlorate.

Moreover, incubation with 15 mM chlorate alone for 24 hours significantly inhibited sulfidogenesis by *D. vulgaris*, as sulfide production was only 49% of the control cells incubated without chlorate (FIG. 5). This result indicates that chlorate at relatively low concentrations has antimicrobial activity against *D. vulgaris*.

Figure 6:
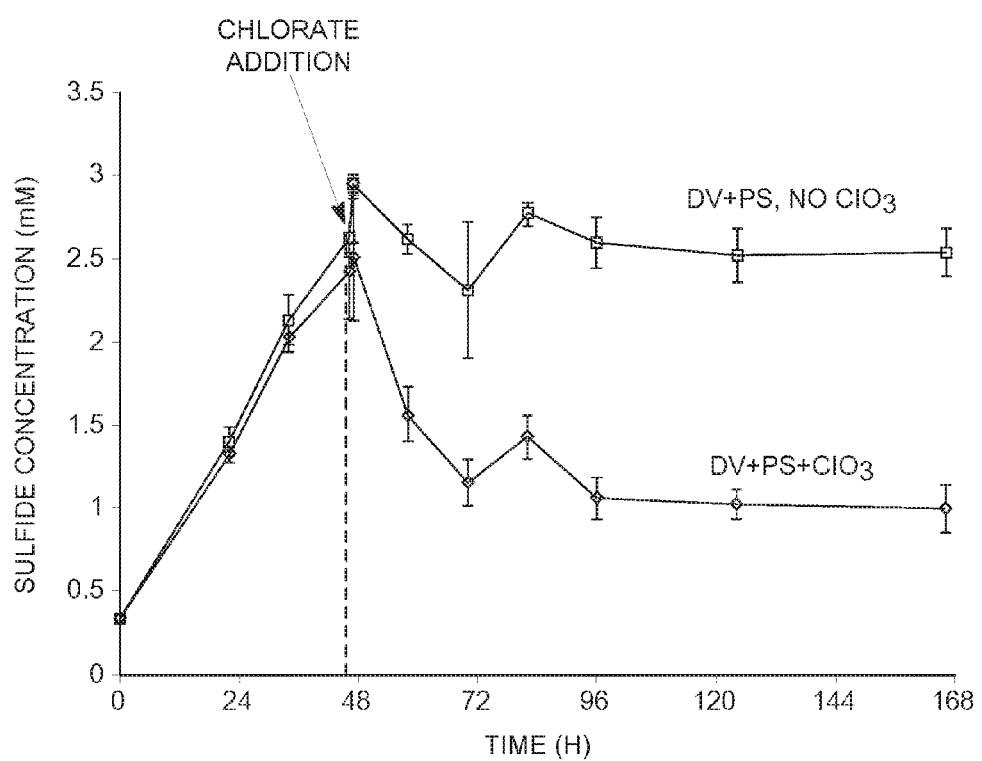
FIG. 6 shows a time course showing inhibition of sulfidogenesis by the SRB *D. vulgaris* (DV) when treated with the (per)chlorate reducing organism *A. suillum* (PS) and chlorate at 48 hours. As can be seen, the treatment results in immediate inhibition of sulfide production and removal of sulfide from the medium relative to the untreated control, which continues to make sulfide.

Additionally, FIG. 6 shows a time course showing inhibition of sulfidogenesis by the SRB *D. vulgaris* (DV) when treated with the (per)chlorate reducing organism *A. suillum* (PS) and chlorate at 48 hours. As can be seen, the treatment results in immediate inhibition of sulfide production and removal of sulfide from the medium relative to the untreated control which continues to make sulfide.

Example 3—Comparative Analysis of the Genomes of Four Species of Perchlorate Reducing Bacteria A comparative analysis of the genomes of four perchlorate-reducing organisms has revealed a genomic island associated with perchlorate reduction. In addition to the characterized metabolic genes perchlorate reductase and chlorite dismutase, the island contains multiple conserved uncharacterized genes possibly involved in electron transport and regulation.

The two key genetic components of the (per)chlorate-reducing mechanism pathway are perchlorate reductase and chlorite dismutase, encoded by the perABCD and cld genes, respectively (21, 23, 28, 43).

The first (per)chlorate-reducing organism to have its genome sequenced was *Dechloromonas aromaticae* strain RCB (26). Recently, draft genome sequences for the perchlorate-reducing organims *Azospira suillum* strain PS (20), *Magnetospirillum bellicus* strain VDY$^T$ (42), and *D. agitata* strain CKB (20, 24) have been characterized (DOE Joint Genome Institute and Eureka Genomics). Additionally, *Dechloromonas* sp. strain JJ, the only member of this genus known to be incapable of reducing either chlorate or perchlorate, was sequenced (Eureka Genomics).

The genera *Dechloromonas* and *Azospira* are both located within the Rhodocyclaceae family of the Betaproteobacteria, from which perchlorate-reducing organisms are frequently isolated (27). In contrast, *M. bellicus* strain VDY$^T$ is a member of the Alphaproteobacteria, and shares 96% 16S rRNA gene sequence identity with the magnetotactic species *M. magnetotacticum* and *M. gryphiswaldense*, despite its apparent inability to form magnetosomes (42) (FIGS. 7 and 8).

Figure 7:
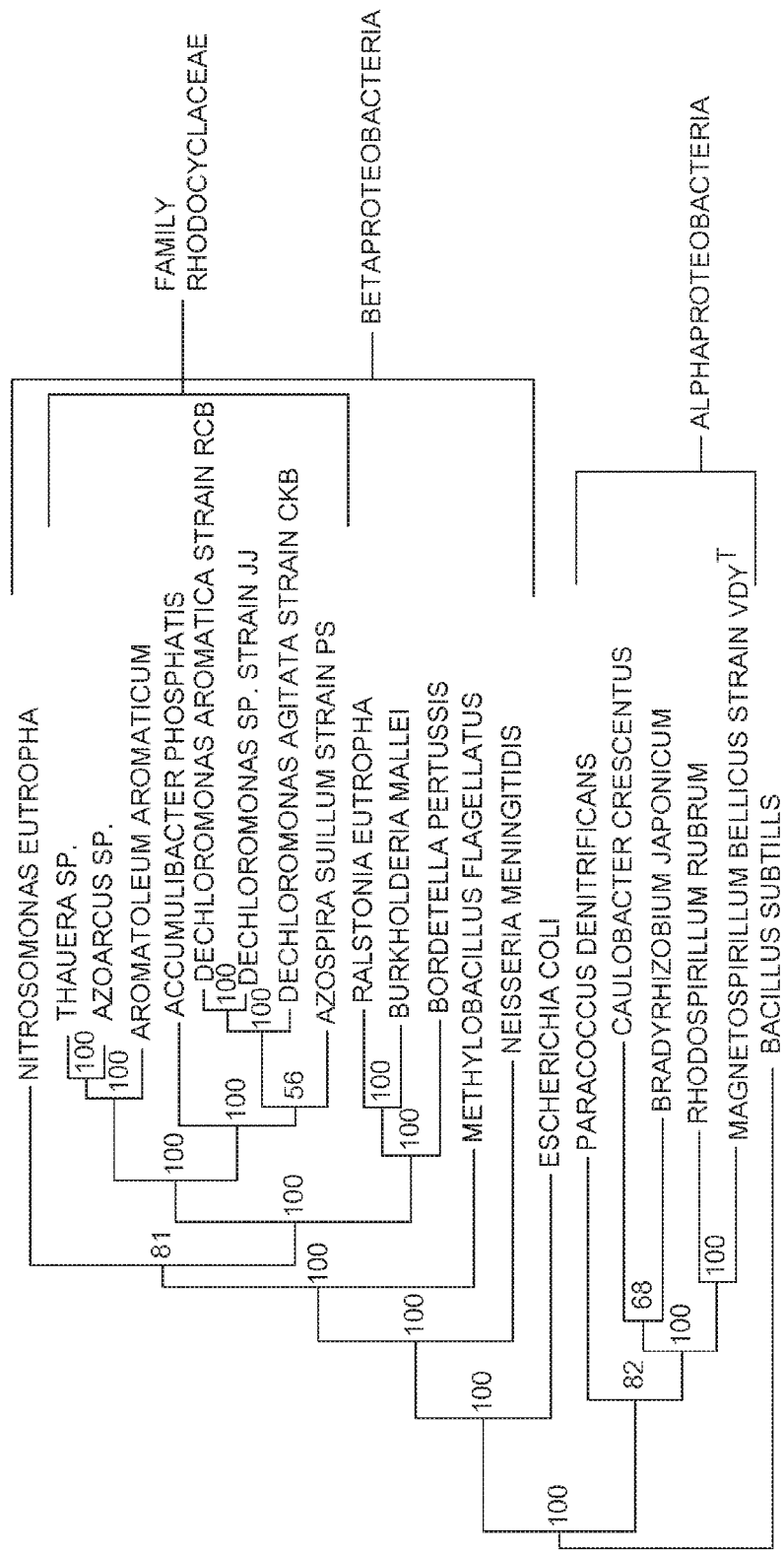
FIG. 7 shows the phylogenetic distribution of genomes of perchlorate reducers. The phylogenetic tree was generated by multilocus sequence analysis using a concatenated alignment of 9 conserved housekeeping proteins (AtpD, DnaA, DnaK, FtsZ, GyrB, RecA, RpoN, SecA, and Srp54). The parameters for the alignment were optimized using ProtTest and the tree was calculated with bootstrap values by phyml (19, 32). The names of perchlorate reducers are identified with a gray background.
Figure 8B:
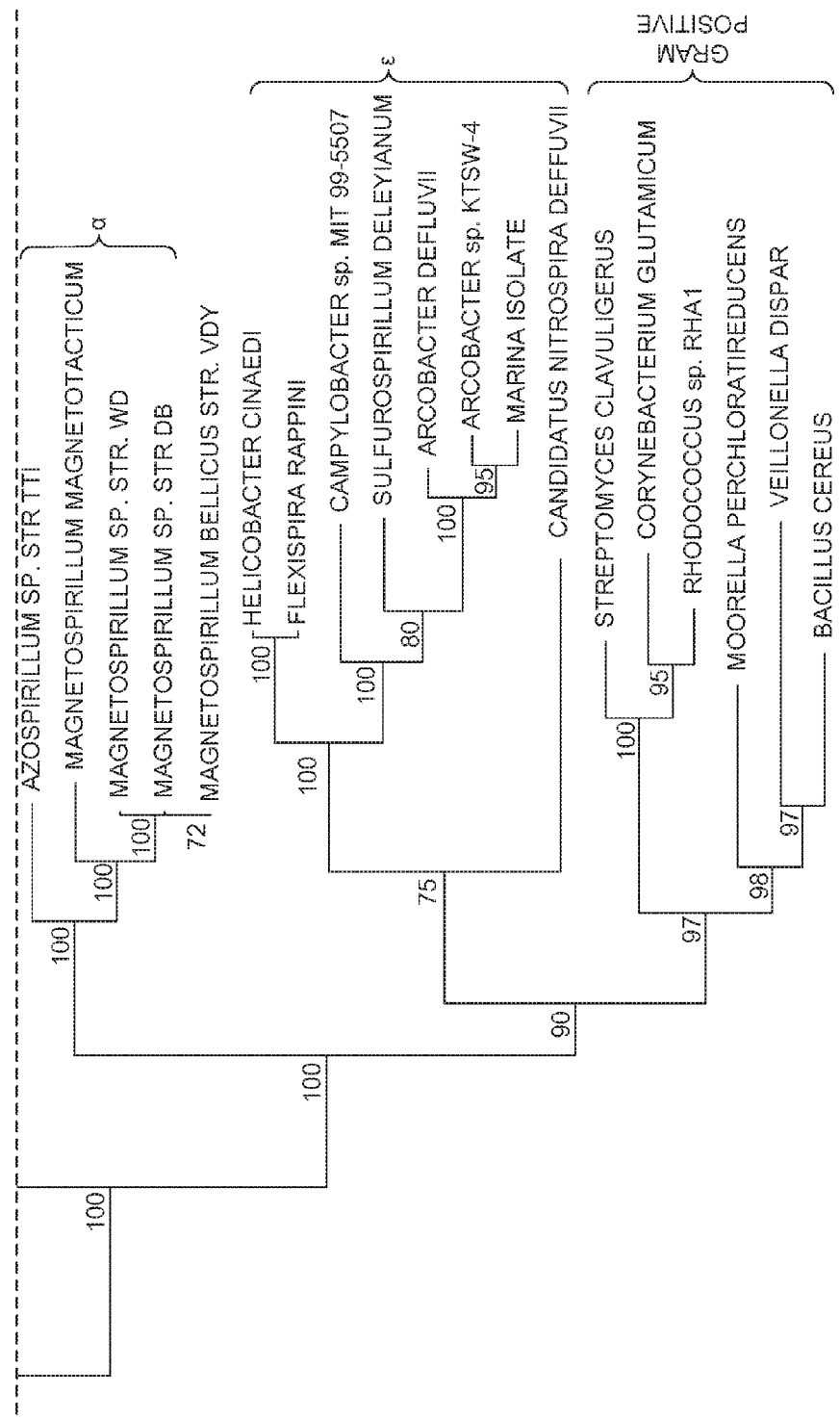
Figure 9:
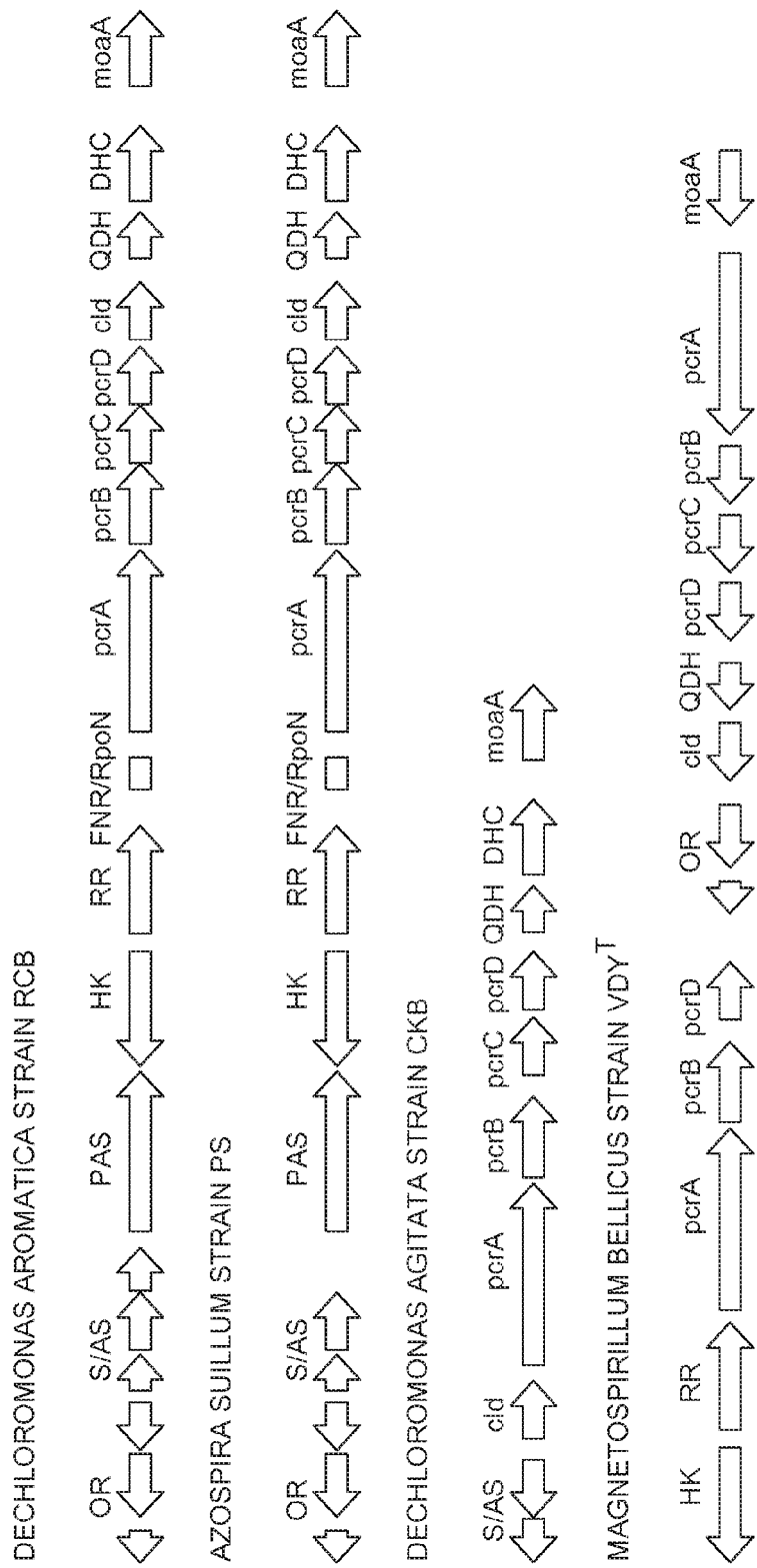
FIG. 9 shows the structure of the conserved core of the perchlorate reduction genomic island (PRI). The conserved genes from four examples of the PRI are depicted. The genes are labeled either with their given gene name, or an abbreviation/acronym for the predicted function of the gene product. perABCD are components/accessory genes of perchlorate reductase, cld is chlorite dismutase, and moaA is a part of the molybdenum cofactor biosynthesis pathway. QDH denotes a gene predicted to encode a membrane-associated tetraheme c-type cytochrome with quinol dehydrogenase activity, while DHC denotes a diheme c-type cytochrome. HK, RR, and PAS represent the histidine kinase, response regulator, and PAS domain sensor of a putative two-component system, while S/AS is a predicted sigma factor/anti-sigma factor system. OR indicates genes annotated as various types of oxidoreductase components, but the substrate and function of their gene products within the context of perchlorate reduction is unknown. FNR/RpoN represents a conserved promoter for perA that contains consensus binding sites for FNR and RpoN.

An initial analysis of the *A. suillum* genome identified several genes adjacent to the genes encoding both perchlorate reductase and chlorite dismutase that were also present in *D. aromatica*, which was unsurprising, given their close phylogenetic relationship (FIG. 7). To examine the complete extent of the synteny surrounding per and cld across all four perchlorate reducers, a simple protein similarity search (phmmer) (30), using the translations of the genes surrounding perA from *D. aromatica* as a query against a database of 1109 curated and finished genomes from HAMAP (38) in addition to the draft genomes of *A. suillum, M. bellicus, D. agitata*, and *Dechloromonas* strain JJ, was performed. Unexpectedly, 17 pairs of similar genes conserved with perfect synteny between *A. suillum* and *D. aromatica* were found. Additionally, a subset of these genes was also found in *D. agitata* (10 genes) and *M. bellicus* (14 genes) (FIG. 9). While in most cases the best-scoring hits from the *D. aromatica* queries were from the other perchlorate reducing organims, there were a few aberrant instances. For example, the gene encoding the molybdopterin biosynthesis, protein A (moaA) homolog in *M. bellicus* had only a moderate degree of similarity to the closely related moaA genes of *D. aromatica, A. suillum*, and *D. agitata*, despite its similar genomic location (FIG. 9). *Dechloromonas* strain JJ did not have high-scoring hits to most of the 17 genes shared by *A. suillum* and *D. aromatica*, and any homologs were non-contiguous, suggesting that there is no comparable genomic region in that organism.

While it has been proposed that cld has a phylogenetic history indicative of lateral gene transfer (22), the nature and extent of such a transfer event was unknown. However, the conservation of ten or more genes among four (per)chlorate reducers leads us to propose that this 10- to 25-kb region constitutes the core of a horizontally transferred (per)chlorate-reduction associated genomic island (PRI).

The definition of this region as a genomic island is justified based on the criteria presented by Juhas et al., some of which is summarized herein (34). Like most genomic islands, the GC content of the PRI is different from the background GC content of the surrounding chromosome (Table 3). While short flanking direct repeats indicative of site-specific integration or homologous recombination have not yet been identified, there is a Pro tRNA gene within 3 kb of the PRI in *A. suillum* and 35 kb of the PRI in *D. aromatica*. This was previously identified as a chromosomal integration site for a phage of *Rhizobium meliloti* (41). In the approximately 35 kb region between the PRI and the Pro tRNA in *D. aromatica*, there are homologs of the F plasmid conjugative transfer genes traIDLEBVFWUNH (33). None of these genes were identified in *A. suillum*, but there are multiple genes in its flanking regions annotated as "phage-associated", suggesting that the PRI may have been historically mobilized by both conjugation and transduction. It is worth noting that a spontaneous mutant incapable of (per) chlorate reduction has never been observed, unlike in other organisms where genomic island integration and excision can be directly observed (29, 31).

tion domain. Moreover, a promoter upstream of perA has been identified that has binding sites for the $\sigma^{54}$ factor RpoN and the regulator of anaerobic metabolism, FNR (39).

This is the first identification of conserved gene families linked with the perchlorate reductase and chlorite dismutase genes in (per)chlorate-reducing organisms. The architecture of the PRI and surrounding chromosomal regions suggests that these genes have been co-transferred, and are completely absent in investigated organisms closely related to (per)chlorate reducers (e.g. *Dechloromonas* strain JJ and *M. magnetotacticum*). These findings imply that the PRI represents a modular metabolism, in that it packages necessary regulatory elements with metabolic genes, in order to facilitate the integration of the horizontally transferred PRI into the host metabolism.

REFERENCES

1. Vance, I. & Thrasher, D. R. in Petroleum Microbiology (eds B. Ollivier & M. Magot) (ASM Press, 2005).
2. Al-Rasheedi, S., Kalli, C., Thrasher, D. & Al-Qabandi, S. in SPE Middle East Oil Show (Society of Petroleum Engineers).
3. [Coates, J. D. & Achenbach, L. A. in Manual of Environmental Microbiology (eds C. J. Hurst et al.) 719-727 (ASM Press, 2001).

TABLE 3

| Organism | *Dechloromonas aromatica* strain RCB | *Azospira suillum* strain PS | *Dechloromonas agitata* strain CKB | *Magnetospirillum bellicus* strain VDY$^T$ |
|---|---|---|---|---|
| Genome Status | Finished | Draft (22 contigs) | Draft (120 contigs) | Draft (324 contigs) |
| Taxonomy (Class) | Betaproteobacteria | Betaproteobacteria | Betaproteobacteria | Alphaproteobacteria |
| Taxonomy (Order, Family) | Rhodocyclales, Rhodocyclaceae | Rhodocyclales, Rhodocyclaceae | Rhodocyclales, Rhodocydaceae | Rhodospirillales, Rhodospirillaceae |
| Genome Size | 4.5 Mb | 3.8 Mb | 4.0 Mb | 8.4 Mb |
| Number of predicted protein-coding genes | 4171 | 3454 | 3957 | 8040 |
| Size of PRI 'core' | 19.1 kb | 19.5 kb | 10.3 kb | 17.6 kb |
| GC Content of Chromosome | 59.2% | 65.3% | 62.9% | 61.5% |
| GC Content of PRI 'core' | 50.9% | 51.2% | 53.4% | 63.2% |
| chlorite dismutase (cld) | Yes | Yes | Yes | Yes |
| perchlorate reductase (pcrABCD) | Yes | Yes | Yes | Yes (pcrABD duplicated) |
| Mo cofactor biosynthesis gene (moaA) | Yes | Yes | Yes | Yes |
| Two-component system | Yes | Yes | No | Yes (missing PAS domain protein) |
| Putative sigma-factor/anti-sigma factor pair | Yes | Yes | Yes | No |
| Unknown oxidoreductases | Yes | Yes | No | Yes (unrelated to RCB/PS genes) |
| Unknown o-type cytochromes | Yes | Yes | Yes | Yes |
| FNR/RpoB pcrA promoter | Yes | Yes | No | No |

The conservation of PRI genes outside of perABCD and cld suggests that there are additional regulatory and metabolic mechanisms involved in (per)chlorate reduction that are un-described. The presence of the molybdenum cofactor biosynthesis cofactor moaA homolog is unsurprising, as perchlorate reduction is dependent on molybdenum, presumed to be due to the use of molybdopterin as a cofactor of PcrA (23, 25). Additionally, there are three conserved families of c-type cytochromes in the PRI, none of which have an experimentally validated function.

There are two separate modules in the PRI that are predicted to regulate the transcription of key metabolic genes, including perA and cld. These two modules consist of a putative σ factor/anti-σ factor pair and a two-component system. The two-component system is of particular interest, as the response regulator contains a $\sigma^{54}$ interaction/activa- 4. Lovely, D. R. & Chapelle, F. H. Deep subsurface microbial processes. Reviews of Geophysics 33, 365-381 (1995).
5. Van Trump, J. I. & Coates, J. D., Thermodynamic targeting of microbial perchlorate reduction by selective electron donors. Isme J 3, 466-476, doi:10.1038/ismej.2008.119 (2009).
6. Coates, J. D., Anderson, R. T. & Lovley, D. R., Anaerobic hydrocarbon degradation in petroleum-contaminated harbor sediments under sulfate-reducing and artificially imposed iron-reducing conditions, Environmental Science and Technology 30, 2784-2789 (1996).
7. Widdel, F. & Bak, F. in The Prokaryotes Vol. 4 (eds A. Balows et al.) 3353-3378 (Springer-Verlag, 1992).
8. Chaudhuri, S. K., O'Connor, S. M., Gustayson, R. L., Achenbach, L. A. & Coates, J. D., Environmental factors that control microbial (per)chlorate reduction, Appl. Environ. Microbiol., 68, 4425-4430 (2002).
9. Bender, K. S., O'Connor, S. M., Chakraborty, R., Coates, J. D. & Achenbach, L. A., The chlorite dismutase gene of *Dechloromonas agitata* strain CKB: sequencing, transcriptional analysis and its use as a metabolic probe, Appl. Environ. Microbiol. 68, 4820-4826 (2002).
10. Cline, J. D., Spectrophotometric determination of hydrogen sulfide in natural waters, Limnol. Oceanogr. 14, 454-458 (1969).
11. Sunde, E. & Torsvik, T. in Petroleum Microbiology (eds B. Ollivier & M. Magot) (ASM Press, 2005).
12. Thrash, J. C. et al., Electrochemical Stimulation of Microbial Perchlorate Reduction, Environmental Science and Technology 41, 1740-1746 (2007); Thrash, J. C. & Coates, J. D., Review: Direct and indirect electrical stimulation of microbial metabolism, Environmental Science and Technology Advance publication (2008).
13. Coates, J. D. et al., The ubiquity and diversity of dissimilatory (per)chlorate-reducing bacteria, Appl. Environ. Microbiol. 65, 5234-5241 (1999).
14. Coates, J. D. & Achenbach, L. A. in Perchlorate, Environmental Occurrence, Interactions, and Treatment (eds B. Gu & J. D. Coates) (Springer Publishers, 2006).
15. O'Connor, S. M. & Coates, J. D., A universal immunoprobe for (per)chlorate-reducing bacteria, Appl. Environ. Microbiol. 68, 3108-3113 (2002).
16. Bender, K. S., O'Connor, S. M., Chakraborty, R., Coates, J. D. & Achenbach, L. A., The chlorite dismutase gene of *Dechloromonas agitata* strain CKB: sequencing, transcriptional analysis and its use as a metabolic probe, Appl. Environ. Microbiol. 68, 4820-4826 (2002).
17. Bender, K. S., Rice, M. R., Fugate, W. H., Coates, J. D. & Achenbach, L. A., Metabolic primers for the detection of (per)chlorate-reducing bacteria in the environment, Appl Environ Microbiol (2004).
18. Coates, J. D. & Achenbach, L. A., Microbial perchlorate reduction: rocket fuelled metabolism, Nature Reviews Microbiology 2, 569-580 (2004).
[19]. Abascal, F., R. Zardoya, and D. Posada. 2005. ProtTest: selection of best-fit models of protein evolution. Bioinformatics (Oxford, England) 21:2104-2105.
20. Achenbach, L., U. Michaelidou, R. Bruce, J. Fryman, and J. Coates. 2001. *Dechloromonas agitata* gen. nov., sp. nov. and *Dechlorosoma suillum* gen. nov., sp. nov., two novel environmentally dominant (per)chlorate-reducing bacteria and their phylogenetic position. Int J Syst Evol Microbiol 51:527-533.
21. Bender, K. S., S. M. O'Connor, R. Chakraborty, J. D. Coates, and L. A. Achenbach. 2002. Sequencing and transcriptional analysis of the chlorite dismutase gene of *Dechloromonas agitata* and its use as a metabolic probe. Appl Environ Microbiol 68:4820-4826.
22. Bender, K. S., M. R. Rice, W. H. Fugate, J. D. Coates, and L. A. Achenbach. 2004. Metabolic primers for detection of (Per)chlorate-reducing bacteria in the environment and phylogenetic analysis of cld gene sequences. Appl Environ Microbiol 70:5651-5658.
23. Bender, K., C. Shang, R. Chakraborty, S. Belchik, J. Coates, and L. Achenbach. 2005. Identification, characterization, and classification of genes encoding perchlorate reductase. J Bacteriol 187:5090-5096.
24. Bruce, R. A., L. A. Achenbach, and J. D. Coates. 1999. Reduction of (per)chlorate by a novel organism isolated from paper mill waste. Environ Microbiol 1:319-329.
25. Chaudhuri, S. K., S. M. O'Connor, R. L. Gustayson, L. A. Achenbach, and J. D. Coates. 2002. Environmental factors that control microbial perchlorate reduction. Appl Environ Microbiol 68:4425-4430.
26. Coates, J. D., R. Chakraborty, J. G. Lack, S. M. O'Connor, K. A. Cole, K. S. Bender, and L. A. Achenbach. 2001. Anaerobic benzene oxidation coupled to nitrate reduction in pure culture by two strains of *Dechloromonas*. Nature 411:1039-1043.
27. Coates, J. D., U. Michaelidou, R. A. Bruce, S. M. O'Connor, J. N. Crespi, and L. A. Achenbach. 1999. Ubiquity and diversity of dissimilatory (per)chlorate-reducing bacteria. Appl Environ Microbiol 65:5234-5241.
28. Coates, J., and L. Achenbach. 2004. Microbial perchlorate reduction: rocket-fueled metabolism. Nature Reviews Microbiology 2:569-580.
29. Dominguez, N. M., K. T. Hackett, and J. P. Dillard. 2011. XerCD-mediated site-specific recombination leads to loss of the 57-kilobase gonococcal genetic island. J Bacteriol 193:377-388.
30. Eddy, S. 1998. Profile hidden Markov models. U.S. Patent 9. Bioinformatics (Oxford, England) 14:755-763.
31. Fukuda, Y., Y. Okamura, H. Takeyama, and T. Matsunaga. 2006. Dynamic analysis of a genomic island in *Magnetospirillum* sp. strain AMB-1 reveals how magnetosome synthesis developed. FEBS letters 580:801-812.
32. Guindon, S., and O. Gascuel. 2003. A simple, fast, and accurate algorithm to estimate large phylogenies by maximum likelihood. Systematic biology 52:696-704.
33. Ippen-Ihler, K. A., and E. G. Minkley. 1986. The conjugation system of F, the fertility factor of *Escherichia coli*. Annu. Rev. Genet. 20:593-624.
34. Juhas, M., J. R. van der Meer, M. Gaillard, R. M. Harding, D. W. Hood, and D. W. Crook. 2009. Genomic islands: tools of bacterial horizontal gene transfer and evolution. FEMS microbiology reviews 33:376-393.
35. Kirk, A. B., P. K. Martinelango, K. Tian, A. Dutta, E. E. Smith, and P. K. Dasgupta. 2005. Perchlorate and iodide in dairy and breast milk. Environ Sci Technol 39:2011-2017.
36. Kounaves, S. P., S. T. Stroble, R. M. Anderson, Q. Moore, D. C. Catling, S. Douglas, C. P. McKay, D. W. Ming, P. H. Smith, L. K. Tamppari, and A. P. Zent. 2010. Discovery of natural perchlorate in the Antarctic Dry Valleys and its global implications. Environ Sci Technol 44:2360-2364.
37. Lawrence, J. E., S. H. Lamm, S. Pino, K. Richman, and L. E. Braverman. 2000. The effect of short-term low-dose perchlorate on various aspects of thyroid function. Thyroid 10:659-663.
38. Lima, T., A. Auchincloss, E. Coudert, G. Keller, K. Michoud, C. Rivoire, V. Bulliard, E. de Castro, C. Lachaize, D. Baratin, I. Phan, L. Bougueleret, and A. Bairoch. 2009. HAMAP: a database of completely sequenced microbial proteome sets and manually curated microbial protein families in UniProtKB/Swiss-Prot. Nucleic acids research 37:D471-8.
39. Munch, R., K. Hiller, A. Grote, M. Scheer, J. Klein, M. Schobert, and D. Jahn. 2005. Virtual Footprint and PRODORIC: an integrative framework for regulon prediction in prokaryotes. U.S. Patent 22. Bioinformatics (Oxford, England) 21:4187-4189.
40. Sanchez, C. A., K. S. Crump, R. I. Krieger, N. R. Khandaker, and J. P. Gibbs. 2005. Perchlorate and nitrate in leafy vegetables of North America. Environ Sci Technol 39:9391-9397.
41. Semsey, S., B. Blaha, K. Köles, L. Orosz, and P. P. Papp. 2002. Site-specific integrative elements of rhizobiophage 16-3 can integrate into proline tRNA (CGG) genes in different bacterial genera. J Bacteriol 184:177-182.
42. Thrash, J. C., S. Ahmadi, T. Torok, and J. D. Coates. 2010. *Magnetospirillum bellicus* sp. nov., a novel dissimilatory perchlorate-reducing alphaproteobacterium isolated from a bioelectrical reactor. Appl Environ Microbiol 76:4730-4737.
43. van Ginkel, C. G., G. B. Rikken, A. G. Kroon, and S. W. Kengen. 1996. Purification and characterization of chlorite dismutase: a novel oxygen-generating enzyme. Arch Microbiol 166:321-326.

I claim:

1. A method of decreasing one or more sulfide-containing compounds in an oil reservoir, the method comprising:
    injecting perchlorate to an oil reservoir comprising sulfate-reducing bacteria,
    wherein the concentration of injected perchlorate is sufficient to decrease sulfate-reducing activity of said sulfate-reducing bacteria, thereby decreasing one or more sulfide-containing compounds in said oil reservoir.

2. The method of claim 1, wherein the oil reservoir comprises sulfate, and wherein the perchlorate is at a concentration that is at least 50% of the concentration of sulfate present in the oil reservoir.

3. The method of claim 1, wherein the oil reservoir comprises sulfate, and wherein the perchlorate is at a concentration that is between 50% and 100% of the concentration of sulfate present in the oil reservoir.

4. The method of claim 1, wherein the method further comprises injecting nitrite.

5. The method of claim 4, wherein the nitrite is injected at a concentration sufficient to inhibit the sulfate-reducing bacteria.

6. The method of claim 4, wherein the nitrite is added in an amount sufficient to yield a perchlorate to nitrite ratio of 100:1.

7. The method of claim 1, wherein the method further comprises injecting sulfate-reducing bacteria with seawater, sediment, or water rich in decaying organic material.

8. The method of claim 1, wherein said one or more sulfide-containing compounds is hydrogen sulfide ($H_2S$).

9. A method of decreasing one or more sulfide-containing compounds in a gas reservoir, the method comprising injecting perchlorate to a gas reservoir comprising sulfate-reducing bacteria, wherein the concentration of perchlorate is sufficient to decrease sulfate-reducing activity of said sulfate-reducing bacteria, thereby decreasing one or more sulfide-containing compounds in said gas reservoir.

10. The method of claim 9, wherein the gas reservoir comprises sulfate, and wherein the perchlorate is at a concentration that is at least 50% of the concentration of sulfate present in the gas reservoir.

11. The method of claim 9, wherein the gas reservoir comprises sulfate, and wherein the perchlorate is at a concentration that is between 50% and 100% of the concentration of sulfate present in the gas reservoir.

12. The method of claim 9, wherein the method further comprises injecting nitrite.

13. The method of claim 12 wherein the nitrite is injected at a concentration sufficient to inhibit the sulfate-reducing bacteria.

14. The method of claim 12, wherein the nitrite is injected in an amount sufficient to yield a perchlorate to nitrite ratio of 100:1.

15. The method of claim 12, wherein the method further comprises injecting sulfate-reducing bacteria with seawater, sediment, or water rich in decaying organic material.

16. The method of claim 12, wherein said one or more sulfide-containing compounds is hydrogen sulfide ($H_2S$).

* * * * *